US 8,453,849 B2

(12) United States Patent
Hamlin et al.

(10) Patent No.: US 8,453,849 B2
(45) Date of Patent: Jun. 4, 2013

(54) ANTI-MICROBIAL MATRIX AND FILTRATION SYSTEM

(75) Inventors: Thomas J. Hamlin, Vernon, CT (US); Mark T. Meyering, Middletown, CT (US); Hemang R. Patel, Middletown, CT (US); Derek A. Daigle, New Haven, CT (US); Robert A. Governal, Tuscon, AZ (US); Rebecca A. Lucht, Cromwell, CT (US); Keith D. Solomon, Cheshire, CT (US); Eshan B. Yeh, Hartford, CT (US)

(73) Assignee: 3M Innovative Properties Company, St. Paul, MN (US)

( * ) Notice: Subject to any disclaimer, the term of this patent is extended or adjusted under 35 U.S.C. 154(b) by 395 days.

(21) Appl. No.: 12/744,392

(22) PCT Filed: Nov. 25, 2008

(86) PCT No.: PCT/US2008/084682
§ 371 (c)(1),
(2), (4) Date: Aug. 23, 2010

(87) PCT Pub. No.: WO2009/070581
PCT Pub. Date: Jun. 4, 2009

(65) Prior Publication Data
US 2011/0006009 A1    Jan. 13, 2011

Related U.S. Application Data

(60) Provisional application No. 60/990,696, filed on Nov. 28, 2007.

(51) Int. Cl.
*B01D 24/00* (2006.01)
(52) U.S. Cl.
USPC .................. 210/503; 210/509; 210/510.1
(58) Field of Classification Search
USPC ................................... 210/503, 509, 510.1
See application file for complete search history.

(56) References Cited

U.S. PATENT DOCUMENTS

| 4,564,456 A | 1/1986 | Homan |
| 4,976,874 A | 12/1990 | Gannon et al. |

(Continued)

FOREIGN PATENT DOCUMENTS

| WO | WO 00/69549 | 11/2000 |
| WO | 2009/070581 | 6/2009 |

OTHER PUBLICATIONS

EP Application No. 08854229.5, Supplementary European Search Report, completed Apr. 8, 2011.

*Primary Examiner* — Chester Barry

(57) ABSTRACT

Provided are an anti-microbial matrix and filtration systems containing the same. The matrix comprises a surface-modified inorganic component and a polymeric binder comprising particles having an irregular, convoluted surface. The surface-modified inorganic component comprises a reaction product of an anti-microbial component and an inorganic component. The anti-microbial component comprises a quaternary ammonium salt containing an epoxide group. A covalent bond is, for example, between the quaternary ammonium cation and a hydroxyl group of the inorganic component. The quaternary ammonium salt can be poly(methyldiallylamine epichlorohydrin). Further, the quaternary ammonium salt can have the formula according to I: (Formula I), wherein n is in the range of 5 to 24. The inorganic component can be diatomaceous earth. The polymeric binder can comprise ultra high molecular weight polyethylene (UHMW PE). Methods of making and using the same are also provided.

(I)

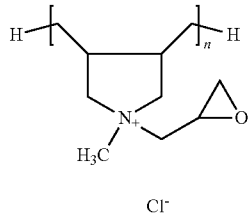

45 Claims, 1 Drawing Sheet

U.S. PATENT DOCUMENTS

| | | |
|---|---|---|
| 6,524,477 B1 | 2/2003 | Hughes et al. |
| 6,715,618 B2 | 4/2004 | Shiau et al. |
| 7,112,272 B2 | 9/2006 | Hughes |
| 7,112,280 B2 | 9/2006 | Hughes et al. |
| 2002/0072545 A1 | 6/2002 | Patil |
| 2003/0006199 A1 | 1/2003 | Shiau et al. |
| 2004/0168973 A1 | 9/2004 | Hughes et al. |
| 2004/0206882 A1 | 10/2004 | Banks et al. |
| 2005/0211635 A1 | 9/2005 | Yeh et al. |
| 2005/0279696 A1 | 12/2005 | Bahm et al. |
| 2007/0075025 A1 | 4/2007 | Patel et al. |
| 2007/0221569 A1 | 9/2007 | Stouffer et al. |
| 2007/0222101 A1 | 9/2007 | Stouffer et al. |

ANTI-MICROBIAL MATRIX AND FILTRATION SYSTEM

CROSS REFERENCE TO RELATED APPLICATIONS

This application is a national stage filing under 35 U.S.C. 371 of PCT/US2008/084682, filed Nov. 25, 2008, which claims priority to U.S. Provisional Patent Application No. 60/990,696, filed Nov. 28, 2007, the disclosures of which are incorporated by reference in their entirety herein.

TECHNICAL FIELD

The present disclosure relates to fluid filtration systems and anti-microbial matrixes uses therein. Specifically, provided are water filtration systems having anti-microbial block matrixes having an active media and a polymeric binder.

BACKGROUND

Filtration of fluids may be accomplished through a variety of technologies, the selection of which is often determined by the contaminant or contaminants that are being targeted for removal or reduction. Particulates are best removed through a process known as depth filtration. The filter collects and holds any dirt or sediment within its matrix. Dissolved organic contaminants appearing on a molecular level may be removed through adsorption or, in the case of minerals and metals, through ion exchange. Very small contaminants, including microorganisms down to sub-micron sizes often require some form of membrane technology in which the pores in the membrane are configured to be smaller than the target contaminant; or they can be deactivated in some manner. Contaminants in drinking water may be broken down into four groups: (i) turbidity and particulates; (ii) organic based chemicals and pesticides; (iii) inorganic matter such as dissolved heavy metals that pose a health risk such as lead; and minerals; (iv) microorganisms such as protozoan parasites, bacteria and viruses.

Each group can be treated with different, specific technologies. A traditional approach to filtration that accommodates multiple types of contaminant groups is to arrange multiple discrete media modules in a linear fashion in separate housings along a path, each module sized in a way to protect sequential stages to the final stage for roughly optimal life of the system. Some filters, however, are designed to treat several contaminant groups through a single filtering technology. The single filtering technology is helpful for applications where highly efficient and compact geometries are warranted, such as in a point-of-use filter for consumers.

For example, serial filtration within a single housing can be achieved wrapping a block filter with single or multiple layers of wrapped or pleated non-wovens or membranes (e.g. U.S. Pat. Appl. Publ. No. 2004/0206882 to Hamlin et al.). These layers are applied to essentially monolithic blocks, with mixed functionality incorporated within the block as a blended monolithic structure. In the case of mixed functionality where a mixture of different active media are employed in the blended monolithic structure, the resultant block has a substantially isotropic pore size distribution, void volume, and geometry—dependent water flow pressure drop for the full depth of the bed. Formulations of these mixed active media blocks are designed with an appropriate trade off between the functionality of one component versus the other, and the cost of the media is affected by the need to select particle size distributions and other media characteristics that result in the best blended performance. As an example, a low cost large particle of activated carbon media (resulting in relatively larger pores in a formed article block) may be sufficient for a chlorine reduction claim. A smaller, higher cost active media particle (resulting in relatively smaller pores in a formed article block) may be required for a cyst claim. The blend of large particles and small particles may create an isotropic pore size distribution that is wider than the individual distributions of either individual component blocks, and may thus be too wide to efficiently retain the cyst. As such, the blended monolithic block may not be as effective in performance for the combination of claims as individual functionality. The engineering trade-off normally employed is to select materials and blend formulations that meet the critical or more difficult claim first, which requires either cost compromise in material, or pressure-drop compromise in the finished monolithic block.

Additionally, the limitations of a mixture of active media include the effect of dilution of mechanism in a mixed system; not all filtration and separation mechanisms are synergistic in their effect. With respect to electrokinetic capture, it is generally believed that a smaller volume having a greater population/concentration of active media functionality can be more effective in acting on a fluid stream than a more dispersed and diluted population of the same particles; especially if the effect of this dilution is to change the geometric relationship between the fluid path and the surface of the particle (by, for example, creating effectively larger pores).

In addition to the aforementioned trade-offs, most commercial blended monolithic blocks are produced using binder particles having undesirable characteristics of melt-flow and coating of active media in neighboring active media particles; this coating may generally result in blinding off some percentage of the surface of the active media.

There is an ongoing need to provide filtration media and systems for highly efficient and compact applications. There also exists a need with regard to depth filter media such as blocks, for a mechanism for reduction of phage, virus, or bacteria that is not dependent on the pore size or pore size distribution of the block; especially where the block pore characteristics cannot effectively reduce a large microorganism such as a cyst.

SUMMARY

Provided are anti-microbial matrixes and filtration systems suitable for compact applications. Methods of making and using the same are also provided. In a first aspect, a separation matrix comprises: a surface-modified inorganic component; and a polymeric binder comprising particles having an irregular, convoluted surface; wherein the surface-modified inorganic component comprises a reaction product of an anti-microbial component comprising a quaternary ammonium salt containing an epoxide group and an inorganic component, and thereby comprising a covalent bond directly between the quaternary ammonium cation and the inorganic component.

Detailed embodiments provide that the polymeric binder comprises ultra high molecular weight polyethylene. Other embodiments provide that the polymeric binder further comprises particles having a generally spherical, non-porous structure. In specific embodiments, the particles having the irregular, convoluted surface have an average particle size in the range of 10 to 100 (or 20-50, or even 30-40) microns. Other specific embodiments provide that the particles having the generally spherical, non-porous structure have an average particle size in the range of 10 to 100 (or 20-80, or even 30-65) microns.

In an embodiment, the quaternary ammonium salt containing the epoxide group has the formula according to I:

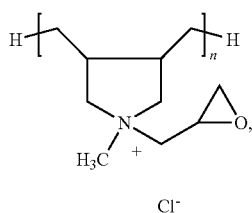

wherein n is in the range of 3 to 250 (or in other embodiments, n is in the range of 5 to 24).

In an embodiment, the surface-modified inorganic component is present in an amount in the range of 60 to 85% by weight and the polymeric binder is present in an amount in the range of 15 to 40% by weight. A detailed embodiment provides that the polymeric binder comprises ultra high molecular weight polyethylene, the particles comprising the irregular, convoluted surface being present in an amount in the range of 10 to 40% by weight of the matrix, and the particles having the generally spherical, non-porous structure being present in an amount of up to 40% by weight of the matrix. In one embodiment, the surface-modified inorganic component has a positive zeta potential at a pH of 9 or greater. In one or more embodiments, the inorganic component is diatomaceous earth.

Certain embodiments include matrixes being effective to provide at least a 4 log reduction of MS-2 phage. In one embodiment, the reduction occurs over a service life of the matrix. In another embodiment, the reduction occurs up to a point of physical plugging of the matrix.

In one or more embodiments, the matrix is free of a cationic metal salt pretreatment. Some embodiments comprise carbon particles having an average diameter of 100 µm.

Another aspect provides a filter element comprising: a housing and a separation matrix located therein; the separation matrix comprising a surface-modified inorganic component and an ultra high molecular weight polyethylene polymeric binder; wherein the surface-modified inorganic component comprises a reaction product of an anti-microbial component according to formula I, wherein n is in the range of 5 to 24 and diatomaceous earth and comprises a covalent bond directly between the cation of formula I and the diatomaceous earth; and wherein the ultra high molecular weight polyethylene comprises particles having an irregular, convoluted surface. In a detailed embodiment, the particles having the irregular, convoluted surface have an average particle size in the range of 10 to 100 microns.

In another aspect, a method of making a sintered porous article comprises providing a base material of diatomaceous earth in a processing tank; providing an anti-microbial component comprising a quaternary ammonium salt containing an epoxide group; agitating the base material in the processing tank substantially simultaneously with spraying the anti-microbial component into the processing tank to form a coated base material; maintaining a ratio of the anti-microbial component to the base material such that the coated base material is below its compaction point; drying the coated base material under vacuum; activating the coated base material, thereby forming a covalent bond between the quaternary ammonium cation and the diatomaceous earth to provide a surface-modified inorganic component; mixing a polymeric binder comprising particles having an irregular, convoluted surface with the surface-modified inorganic component; filling a mold with the mixture of the particles having an irregular, convoluted surface and the surface-modified inorganic component to form a matrix; and heating the matrix to point-weld the polymeric binder to the surface-modified inorganic component and to form the porous sintered article.

A further aspect provides a separation media comprising activated carbon and a reaction product of a quaternary ammonium salt containing an epoxide group having the formula according to I, wherein n is in the range of 3 to 250 and diatomaceous earth, wherein the reaction product has a covalent bond directly between the quaternary ammonium cation and the diatomaceous earth. In a detailed embodiment, n is in the range of 5 to 24, and wherein the reaction product maintains a positive zeta potential for at least one month.

Another aspect including methods of filtering water, the methods comprising providing a filter matrix comprising a surface-modified inorganic component; and a polymeric binder comprising particles having an irregular, convoluted surface; wherein the surface-modified inorganic component comprises a reaction product of an anti-microbial component comprising a quaternary ammonium salt containing an epoxide group and an inorganic component, and thereby comprising a covalent bond directly between the quaternary ammonium cation and the inorganic component; and passing water through the matrix.

Also provided are zoned filtration systems having anti-microbial matrixes suitable for compact applications. Methods of making and using the same are also provided. In a first aspect, a filtration system comprises at least a first zone and a second zone, wherein the first zone comprises: a surface-modified inorganic component; and a polymeric binder comprising particles having an irregular, convoluted surface; wherein the surface-modified inorganic component comprises a reaction product of an anti-microbial component comprising a quaternary ammonium salt containing an epoxide group and an inorganic component, and thereby comprises a covalent bond directly between the quaternary ammonium cation and the inorganic component.

In an embodiment, the second zone comprises a surface sieve, a depth sieve, a chemical adsorption matrix, a chelation matrix, a catalytic matrix, or combinations thereof. In another embodiment, the first zone and the second zone are annularly concentrically disposed to each other. In a detailed embodiment, the second zone surrounds the first zone. Provided in another detailed embodiment is the first zone and the second zone being layered.

In one or more embodiments, the second zone is located at an upstream portion of the filtration system and the first zone is located at a downstream portion of the filtration system.

In another aspect, provided are filtration systems comprising a first concentric zone and a second concentric zone surrounding the first concentric zone, the first zone comprising: a surface-modified inorganic component and a first polymeric binder comprising particles having an irregular, convoluted surface; wherein the surface-modified inorganic component comprises a reaction product of an anti-microbial component comprising a quaternary ammonium salt containing an epoxide group and an inorganic component, and thereby comprises a covalent bond directly between the quaternary ammonium cation and the inorganic component; and the second zone comprising an adsorptive component and a second polymeric binder. A detailed embodiment provides that the second polymeric binder comprises particles having an irregular, convoluted surface. In another embodiment, the first polymeric binder comprises ultra high molecular weight polyethylene.

In one or more embodiments, the adsorptive component of the second zone comprises activated carbon and the second polymeric binder comprises ultra high molecular weight polyethylene. Additional embodiments may further comprise a third zone surrounding the second zone, wherein the third zone comprises a surface sieve. Still other embodiments may further comprise a third zone surrounding the first zone, wherein the first zone comprises a surface sieve.

A further aspect provides methods of filtering water comprising providing a filtration system comprising at least a first zone and a second zone, wherein the first zone comprises: a surface-modified inorganic component; and a polymeric binder comprising particles having an irregular, convoluted surface; wherein the surface-modified inorganic component comprises a reaction product of an anti-microbial component comprising a quaternary ammonium salt containing an epoxide group and an inorganic component, and thereby comprises a covalent bond directly between the quaternary ammonium cation and the inorganic component; and passing water through the filtration system.

Before describing several exemplary embodiments of the invention, it is to be understood that the invention is not limited to the details of construction or process steps set forth in the following description. The invention is capable of other embodiments and of being practiced or being carried out in various ways.

DETAILED DESCRIPTION

Provided are filtration systems suitable for compact applications that rely on electrokinetic adsorption (such as an antimicrobial media for POU water filtration) and that substantially avoid premature failure in an environment containing contaminants that can both interfere or compete with the adsorptive capability, and prematurely plug the end-stage unit by cake formation or pore occlusion. The combination of a highly charged cationic surface modified separation media with convoluted plastic binding particles provides a matrix that is capable of trapping and retaining microbiological contaminants much smaller than the apparent size of the fluid paths within the sintered pore structure.

In one aspect, provided is an arrangement of annular concentric filtration zones, optimized for removal of contaminants at discrete locations, arranged to provide enhanced life, reduced differential pressure, high efficiency and reliability, and enhanced protection of downstream filtration mechanisms in sequential zones.

Filtration systems in one or more embodiments are arranged as a series of cylinders within cylinders, the cylinders are filtration devices can be produced by methods disclosed in U.S. Pat. Nos. 6,524,477 and 7,112,280 (Hughes et al.), each of which is incorporated herein by reference in their entireties, or optionally are filtration devices as disclosed in co-pending U.S. Pat. Appl. Publ. No. 2005/0279696 (Bahm et al.). Each cylinder constitutes a separate zone, and each is formulated to meet a specific need or a combination of complimentary needs; and arranged to optimize the functionality of either the most critical need or the most costly components which service the critical need, in the most beneficial sequence. Benefits can include longest system life, highest efficiency, lowest cost, or lowest pressure drop, as required in the specific application. By the application of engineering design principles, simultaneous optimization of benefits can be realized in these systems by manipulation of individual zone geometries to achieve high performance zones with known empty bed contact times, simplified formulations, and well controlled characteristics. In an embodiment, the filter is capable of effectively reducing a mixture of health and aesthetic contaminants, including bacteria and virus to levels required by the (California EPA) for supplemental devices such as under-the counter residential home water filters, and refrigerator mounted water dispenser filters.

Figure 1:
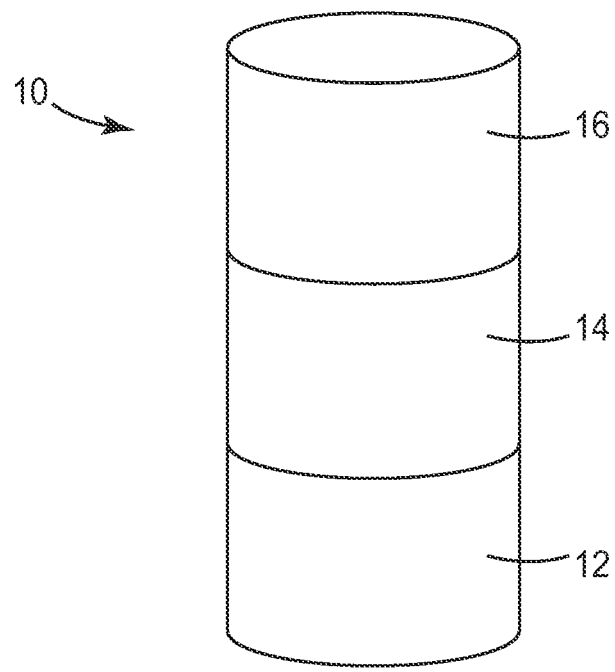
FIG. 1 is a schematic of a multi-zoned filtration device arranged in a layered configuration.
Figure 2:
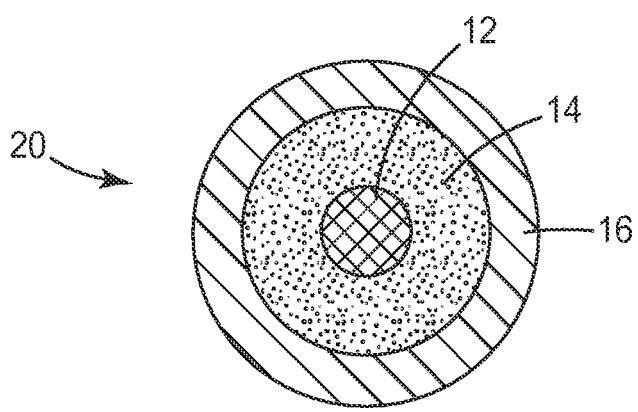
FIG. 2 is a schematic of a multi-zoned filtration device arranged in an annular, concentric configuration.

With reference to FIG. 1, an exemplary filtration system 10 is provided having three zones arranged in a layered configuration, where a first zone 12 comprises antimicrobial technology; a second zone 14 comprises organic adsorption technology; and a third zone 16 comprises sieve technology. In FIG. 2, another exemplary filtration system 20 is provided, where the zones are arranged in an annular concentric configuration, where a first zone 12 comprises antimicrobial technology; a second zone 14 comprises organic adsorption technology; and a third zone 16 comprises sieve technology.

In another aspect, provided is a filter matrix comprising a highly charged cationic surface modified separation media (active media) material combined with binder plastic particles include convoluted particles to form a sintered porous article having enhanced electrokinetic adsorptive capability. This matrix includes the highly charged separation media (active media) bound in a matrix of a sufficient amount of discrete convoluted plastic particles which have point-welded with the separation media (active media) to produce a filter matrix; the matrix being porous, having low pressure drop in service application, and being able to trap and retain microbiological contaminants much smaller than the apparent size of the fluid paths within the sintered pore structure. Binder is selected to take advantage of both point welding and convolution of the binder structure. The term point-welded is used to describe the bonding relationship between a binder particle such as UHMW PE to a neighbor particle; the neighboring particle could be another binder, or an active media particle, or a structural member. An individual particle may be bonded simultaneously to multiple surrounding particles, by multiple point welds. UHMW PE binder particles are able to soften only at the surface of the particle during a high temperature sintering step, over a reasonably broad range of temperatures. The surface becomes tacky, and will stick to an adjacent particle at the point of contact. This is in contrast to a lower density particle, which soften at generally lower temperatures, and will more readily melt and flow over the surface of an adjacent (non melting) particle. Further, the UHMW PE retains its basic morphology during the sintering step, i.e. a convoluted particle remains convoluted per the descriptions provided in U.S. Pat. No. 7,112,280 (Hughes et al.).

In a further aspect, provided is a block formed from an electrokinetically active quaternary amine, such as a polydiallyl amine epichlorohydrin polymer, which is covalently bonded to inorganic diatomaceous earth as the primary functional active media and a small size convoluted UHMW PE binder particle. This block can be used as a discrete zone in an arrangement of annular concentric filtration zones, the zones being arranged in a manner optimized for removal of contaminants at discrete locations, as well as to provide enhanced life, reduced differential pressure, high efficiency and reliability, and enhanced protection of downstream filtration mechanisms in sequential zones. This block can be produced using the methods disclosed in U.S. Pat. Nos. 6,524,477 and 7,112,280 (Hughes et al.), both of which are incorporated herein by reference in their entireties. In one or more embodiments, the block comprises a highly charged cationic surface modified diatomaceous earth filler material, such as one described in U.S. Pat. Appl. Publ. No. 2005/0211635 (Yeh et al.), hereby incorporated by reference in its entirety, where charge is demonstrated via zeta potential/streaming potential, combined with binder plastic particles to form a sintered porous article having enhanced electrokinetic adsorptive capability. By incorporating this type of block into the multizone annular concentric filtration zone device, an effective mechanism is present which is capable of 4-log viral reduction, and 6-log bacterial reduction as specified in the California EPA protocol.

The following define specific terms, as they are understood to be used in the present disclosure.

Reference to "quaternary ammonium salt" means salts of quaternary ammonium cations with an anion. Quaternary ammonium cations, also known as quats, are positively charged polyatomic ions of the structure NR4+ with R being alkyl groups. Unlike the ammonium ion NH4+ itself and primary, secondary, or tertiary ammonium cations, the quaternary ammonium cations are permanently charged, independent of the pH of their solution. One exemplary quaternary ammonium salt containing an epoxide group is represented by Formula I, below. Note that for stability purposes, the quaternary ammonium salt is shipped in hydroxyl format, and that the epoxide group is expressed once an activating agent, such as a caustic material, is applied.

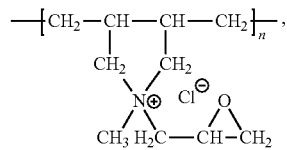

where n is between 3 and 250 (in other embodiments n is in the range of 5 to 24).

The term "particles having an irregular, convoluted surface" refers to particles of unique morphology as set forth in U.S. Pat. No. 7,112,272 (Hughes et al.), hereby incorporated by reference in its entirety, which, when compared to particles of substantially spherical shape, show higher surface areas and lower bulk density.

"Annular concentric" means a nested arrangement of cylinders, each cylinder having non-overlapping outer diameters and inner diameters, all with a common center point. When viewed from the top (or in cross section), such an arrangement would appear as a series of annuli. An annulus is a figure bounded by and containing the area between two concentric circles.

The term "layered" as used to describe positions of two or more filtration zones means the zones are arranged axially, that is the zones have substantially overlapping outer diameters and inner diameters.

An "upstream portion" of the filtration system is the axial area extending from the location where water or the material to be filtered enters the system to a location partway down the system (i.e., ¼, ⅓, ½ of the length of the filter) and a "downstream portion" is the axial area extending from the location where water or the material to be filtered exits the system to a location partway down the system (i.e., ¼, ⅓, ½ of the length of the filter).

"Fluid filter media" refers to the component(s) of a filtration or separation article that perform an active role in removal of contaminants by virtue of their physical properties or surface chemical properties. The media is typically a particle or combination of particles, or fibers, that have an active role and mechanism in mechanical, chemical reactive, chemical adsorptive electrochemical adsorptive, or chelation (and other filtration/separation mechanisms known in the art). Representative fluid filter media include, but are not limited to activated carbon (AC), diatomaceous earth (DE), powders of polyethylene, fibers of polyethylene and polypropylene, and a lead adsorption component such as titanium silicate (ATS, Engelhard Corp, Iselin, N.J.). Both AC and DE are active media and are major fluid filtration components, as they allow fluids, such as, for example, water to flow through and mechanically separate and/or adsorb undesired species present in influent fluid, such as, for example, water used for drinking purposes, from being present in the effluent fluid stream by at least one or more of the following mechanisms: mechanical sieving, adsorption and charge interactions.

A wide variety of methods and numerous resources are used to supply DE, resulting in diversity in both physical and chemical characteristics. DE is a naturally occurring material, composed of skeletal remains of single-celled plants called diatoms. In the diatoms' lifetimes, the diatoms abstract silica and other minerals from water, and when the diatoms die, only the diatoms skeleton shapes remain. Since DE has a mixture of minute particles of different size, shape and structure, it has been used for many years as a filter media or as a filter aid. The composition of un-processed DE is mostly silica, with some alumina, calcium oxide, iron oxide, titania, etc. Despite its compositional complexity, the surface of DE is covered with hydroxyl groups when in a moisturized environment. The present disclosure describes, among other features, the use of such surface hydroxyl groups to react with charged antimicrobial species so as to charge modify the surface to process antimicrobial ability. It is believed that activated carbon, polymers, ceramics, and transition metals once treated, if necessary, to generate surface hydroxyl groups, may also be reacted in this way to generate antimicrobial activity.

A commercially available un-processed DE is sold under the tradename Celite 501. DE sold under the tradenames Celpure S 1000 and S300 (available from Advanced Minerals of Santa Barbara, Calif.) are pre-processed to remove metal content and very fine micro-sized particles.

"Fiber" is a particle having an aspect ratio greater than approximately 2:1 (length to width).

"UHMW PE" or "UHMWPE" refers to ultra high molecular weight polyethylene.

"Point-welded" refers to the binding mechanism of the surface of one object to another object at a discrete point. In this application, point-welded is used to describe the bonding relationship between a binder particle such as UHMW PE to a neighbor particle; the neighboring particle could be another binder, or an active media particle, or a structural member.

"Fail-safe mechanism" means a mechanism that ensures that the final filter maintains its contamination-reduction capability until the end of the design life of the final filter.

"Antimicrobial filter" means a filter that reduces the concentration of microorganisms (including viruses, bacteria, and cyst) in a fluid.

"Adsorption" means the ability of certain solids to preferentially concentrate specific substances from a solution onto its surface, for example, intermolecular forces of attraction between solid and substance adsorbed (Vander Waals attraction).

"Size-exclusion" means the filtration mechanism in which the contaminants of size larger than the pore-size of the filter are removed from the filtration stream simply because they cannot squeeze through the filter-pores.

"Mechanical-interception" means the filtration mechanism in which contaminants flowing in a fluid stream are intercepted by the solid-matrix of a filter and the flow of the contaminants is slowed or stopped, eventually leading to capture of the contaminant even though the size of the contaminant may be smaller than the size of the pores in the filter.

"Significantly reduce fluid flow" means to reduce flow to about 5% of the initial flowrate or the rated flowrate.

"Coagulation" means the process of formation of semi-solid lumps in a liquid. Coagulation generally results in increased viscosity of the liquid.

"Total organic carbon (TOC)" means the amount of carbon covalently bonded in organic molecules. Polyanionic acids like humic and tannic acids are sources of TOC.

Reference to "impulse filling" means that a force is applied to the mold, causing a discrete, substantially vertical displacement that induces movement of at least a portion of the particles in the mold, causing the particles to assume a compact orientation in the mold. This includes indirect methods such as hammer blows to a table to which the molds are clamped and impacts to the table from a pneumatic cylinder, and any suitable direct methods that displace the molds with a series of jarring motions. In some embodiments, the impulse filling comprises a series of discrete displacements (i.e., impulses) applied to the mold. Impulse filling differs from vibration in that there is a period of non-movement or of little movement between the displacements. The period between displacements is typically at least 0.5 (in some embodiments, at least 1, 2, 3, 5, or even at least 10) seconds. The displacement applied to the mold has a vertical component. In some preferred embodiments, the vertical component (as opposed to the horizontal component) accounts for a majority (in some embodiments, a substantial majority (>75%), or even nearly all (>90%)) of the molds movement.

The term "compaction point" refers to a physical condition of a liquid/solid mixture that generally relates to the behavior of the solid particles of the mixture in the presence of the liquid. Below (or before) the compaction point, the mixture will dry to a fluffy powder. Above (or past) the compaction point, the mixture will dry to a solid mass.

With regard to retaining very small contaminants, such as phage measuring in the range of approximately 20 to 60 nm, mean pore flow of the filter matrix is one consideration. In one or more embodiments, however, the combination of active media, for example, charge-modified DE, with convoluted UHMW PE provides a matrix that is capable of trapping and retaining microbiological contaminants much smaller than the apparent size of the fluid paths within the sintered pore structure. Generally, the mean particle size (d50), defined as the size in microns at which 50% of the sample is smaller and 50% of the sample is larger, of the components of the media, e.g., charge-modified DE and convoluted UHMW PE, is substantially greater than 10 µm (or even 5 µm), the mean physical spacing (defining a fluid path) between particles will generally not be substantially submicronic in scale. That is, the physical spacing between particles defining a pore size will not be substantially less than 0.5 microns. Measurements of apparent pore size on structures made with non-charge modified DE media and convoluted UHMW PE show Mean Flow Pore (MFP) between 0.5 and 1.5 microns, which is both formulation- and block-geometry-dependent. The MFP measurement was obtained from a PMI Capillary Flow Porometer, modified to hold portions of cylindrical filter candles of 1.5" OD and 0.375" ID, with pressure and flow radially conducted from OD to ID.

Generally, small active media particles require small binder particles to produce blocks with high active media loading and acceptable handling strength. Additionally, the morphology of the binder polymer affects the handling strength and the active media loading characteristics, as discussed in U.S. Pat. No. 7,112,280 (Hughes et al.). Using DE as a media, the potential for loading the maximum percentage of media is decreased as media particle size decreases, to maintain a high handling strength. Using convoluted UHMW PE binder particles adds strength at a given percentage of media when it is substituted for a standard UHMW PE spherical binder. A formulation that contains a high percentage of media will have pore size characteristics that are highly dependent on the interstitial spacing properties of the media and the packing method, and less affected by the binder. A formulation that contains a low percentage of media will have a higher contribution of the binder to the pore size characteristics. The use of highly convoluted binder particle provides a better ability to bind fine particles, such as DE.

The influence of media particle size on apparent pore size indicates that the practical limitations on physical pore size are greatly influenced by both raw material selection and processing. It is believed that to create a block having a pore size exclusion mechanism suitable for protection against virus would require either raw materials of diminutive size, or a process using conventional raw materials which greatly compresses overall porosity and pore volume. Such a process and materials would create blocks having relatively high pressure drop at service flow rates. At extreme compression, the beneficial effects of convoluted binder polymer would be diminished; particularly the benefit of managing the void spacing provided by the preferred convoluted binder.

Interactions between media particle size, binder particle size, morphology, fabrication process, resultant structure, and test methods result in apparent pore size data that often does not accurately predict microorganism size exclusion capability of a block. As a result, microbiological challenge data is usually needed to characterize antimicrobial capability of the filter system. For example, to determine whether a filter matrix is suitable to achieve an effective minimum 4-log reduction of phage and virus (0.005-0.1 micron), a sieving or mechanical size-exclusion removal mechanism alone, especially at nominal pore sizes in excess of 1 micron, is not sufficient to ensure highly effective removal of virus.

The use of the convoluted UHMW PE provides a larger void volume relative to a non-convoluted homologue, high active media loading, and generally more flow paths, and opportunity for contaminant to find active adsorptive surface while flowing through the structure. The result is low pressure drop with efficient removal under the conditions of the service application The use of the covalently bonded quaternary amine as a surface modification to DE provides the highly charged cationic surface contained in the cationic surface modified separation media zone which is included in one embodiment of an annular concentric filtration device.

Using a filter matrix of convoluted UHMW PE with surface-modified DE shows that there is substantially low effective reduction of MS-2 with an un-modified DE bound in a polymer matrix. It is believed that the mechanism of enhanced capture at equivalent porosity is primarily dependent on the presence of the covalently bonded quaternary amine as a surface modification to DE. It is believed that the capture mechanism is electrokinetic adsorption. The quaternary amine which is covalently bonded to the surface of the DE is capable of providing a significantly greater viral reduction than the un-modified DE. The unique combination of preferred active media with convoluted UHMW-PE has proven to be sufficient in and of itself to provide an efficient electrokinetic capture, demonstrated by reduction of microbiological contaminant MS-2 Phage.

Another unique aspect of this invention is the utility of this electrokinetic capture with the challenge solution used to test the efficiency; this being MS-2 phage in a humic or tannic acid solution. Effective filtration has been achieved without the use of a soluble metal salt pretreatment to modify the surface surrounding the quaternary amine. As a result, the ability of such a filter to remove MS-2 particles, and function effectively in the presence of an organic acid load has been demonstrated by using the cationic surface modified separation media zone alone in a tannic acid environment. In addition, the ability of the surface modified separation media zone of the present invention to remove MS-2 particles in a humic acid environment has been demonstrated in combination with a sleeve style prefilter as a first zone, followed by the cationic surface modified separation media zone as a second zone, to produce the present inventive annular concentric filtration device. Surprisingly, the cationic surface modified separation media zone when tested alone without a first zone sleeve-style prefilter was found to plug prematurely in either the humic acid or the tannic acid test environment. Such plugging occurs without loss of antimicrobial functionality, thus demonstrating 1) plugging without the need for a precipitated metal salt adjunct, and 2) sufficient capacity and effective adsorption of virus in the polyanionic acid TOC environment. Without wishing to be bound by theory, it is believed that the polyanionic acid exists in the challenge solution test environment as both a dissolved component and a colloidal component. Both must be removed, along with the MS-2 particles in the seeded challenge solution. It appears that the colloidal component of the polyanionic acid is the plugging portion of the challenge solution, while the dissolved component competes with the microbiological contaminants for active sites on the cationic surface modified separation media. There is a possibility that an interaction between microbiological contaminants (including MS-2) and polyanionic acids exists, such that colloid is formed or generated when these species are in fluid contact with each other. However, this interaction does not deactivate the microbiological activity of the MS-2 contaminant, since it is clear that the seeded challenge test solution applied to a filter block containing a non-active media such as unmodified DE will plug as well, while allowing free passage of microbiologically active MS-2. The use of an appropriate prefilter such as a first zone sleeve, with a moderate colloid reduction capability and optionally additional chemical removal capability can be thus used to tune the performance of a system, by optimizing the volume of TOC—adjusted fluid that passes through the second zone prior to plugging; and prior to exhausting the electrokinetic capacity of the present inventive discrete zone filter. As an example, the first zone prefilter sleeve can be configured as a fail safe mechanism in one of several designs. One design would be to reduce a certain amount of the colloid burden to enhance the life of the cationic surface modified separation media zone, but allows enough of the colloid burden to pass and plug the cationic surface modified separation media zone at a predetermined volume of seeded challenge test solution. An alternative design would be to reduce a substantially larger portion of the colloid burden, to the point where the first zone becomes the plugged zone, at a predetermined volume of challenge water. The alternative design is the subject of U.S. Pat. Appl. Publ. No. 2007/0075025 (Patel et al.) which is incorporated herein by reference.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

While the specific examples and details of the present disclosure relates to microbial reduction in water, it is believed that the technical principles and the specific chemical concepts discussed herein will most likely apply to microbial reduction in the gas phase as well. Thus, whenever the term fluid is used in the present disclosure, it is understood to mean fluid in the conventional sense including liquids, such as for example, water and gas, such as for example, air.

EXAMPLES

Sintered Blocks Procedure

A general procedure is employed to produce sintered blocks by the methods of U.S. Pat. Nos. 6,524,477 and 7,112,280 (Hughes et al.). The general procedure is applicable to blocks formed from all types of fluid filter media, for example, carbon blocks; blocks containing the combination of an electokinetically active quaternary amine which is covalently bonded to inorganic diatomaceous earth as the primary functional active media, combined with convoluted UHMW PE binder particles; and zoned blocks having zones of different functionalities.

General procedure: fluid filter media are pre-blended in a mixing vessel appropriate to the batch size to be produced, such that there is a homogeneous blend of all components. The blended components are added to a metal mold of nominal dimensional shape, suitable for heating. Other lengths can be produced as needed for specific applications. The mold is filled with the blended powder under conditions of vibration (classical vibration, or impulse vibration as described in both U.S. Pat. Appl. Publ. Nos. 2007/0222101(Stouffer et al.) and 2007/0221569 (Stouffer et al.), both which are incorporated herein by reference), to eliminate air and assist the settling and packing of powder in the mold. The filled mold may also be compressed longitudinally to a desired packing density, length, and resultant block density. The mold is then sealed.

Once filled, packed and sealed, the mold is heated to a temperature of nominally 177° C.+/−3° C. for a period of approximately 1 hour. Heating time and temperature ramp/soak conditions can be adjusted as needed to effect complete sintering of the block, by routine experimentation.

Generally, the molds are allowed to cool prior to block ejection from the mold. For example, molds can be placed on a cooling rack for a time sufficient to cool to room temperature. Or cooling liquid can be forced through channels in the mold. The mold design impacts the choice of cooling method. Of interest is that blocks made by this method have been ejected hot from the mold, within the first minute or two of removal from the heat source, and allowed to cool free standing, with no visible penalty in block integrity and shape, or weight. Hot blocks require special handling, as it is believed that they would be somewhat vulnerable to deformation or damage in handling while hot; as such, the blocks reported in these examples have all been allowed to cool to at or near room temperature prior to ejection.

After cooling and ejection, the blocks can be safely handled, measured and further processed. The blocks can be further machined to exact dimensions (ID, OD, length) or shaped as required, for fit into a variety of housings or adapters. This is a useful feature in that the mating surfaces of an annular concentric filtration multi zone block can be formed to correct diameters, or machined to close tolerances. The internal pore structure of these blocks is generally isotropic; having substantially the same pore size and density at all points from top to bottom, inner diameter to outer diameter, and at each respective surfaces. As such, a block with machined surfaces will have generally the same filtration characteristics as a block with formed surfaces; since there is generally no appreciable gradient going from one surface to another. A zone is substantially self-consistent through its filtration depth.

For demonstration blocks, raw blocks between 5" and 8" in length are formed. After ejection of the blocks, they are trimmed as necessary to a standard length. In a full production system, the length would be closely controlled by precise filling of designed molds, to minimize waste and processing steps.

In anticipation of forming a hybrid annular concentric filtration zone system where the carbon block is first zone sleeve surrounding a second zone of antimicrobial core, the ID of the carbon block of the present example is machined to provide a slip fit to the anticipated diameter of the core. In a full production system, the carbon block ID would be controlled by mold and mandrel design; again to minimize waste and processing steps.

Block physical dimensions are measured, and normalized to a weight per unit length of the correctly dimensioned article, as a basis for comparison, and to provide engineering data for scale-up. The blocks at this point are double open ended.

To collect data on such blocks, end caps are applied to seal the top and bottom of the block. The top end cap generally has an outlet of suitable configuration for adapting to a housing (for example, a threaded fitting or a straw style tube for compression fitting in a suitable receptacle). The bottom end cap is generally a solid disc plate, with no outlet. End caps are applied using a hot melt glue, as is known in the art.

Optional modifications to the preparation of the blocks can enhance the consistency and strength of the blocks. For example, indexing washers inserted after filling on the top of the column of powder, and pushing down the washer on top of the column of powder using an air cylinder for compression to enhance structure, cosmetics, and provide another means of controlling finished block packing density. Also, the inclusion of a small additive amount of a large particle (such as a nominally 100 micron d50 carbon particle) has the benefit of providing a reinforcement bar effect, further improving structure and cosmetics. Other particles that likely perform the same function. may be organic polymeric materials, or inorganic particulate in nature. Additionally, sifting the active media to remove any large coalesced particles prior to blending provides further benefits. It has been noted that the large sifted retain particles can be re-ground to small active media particles, to enhance recovery and yield.

Microbial Challenge

The microbial challenge set forth below is a simulation of the first 16 days of the EPA challenge testing "Guide Standard and Protocol for Testing Microbiological Water Purifiers" (April 1987) modified to achieve a Supplemental Device Claim through California Department of Health Services (DHS)), in which multiple cycles of two separate seeded challenge liquids are sequentially flowed though a test filter over a two-day period. This is referred to as a "2-day test."

An initial flow rate is established during initial wetting of the test filter, using clean, dechlorinated tap water; the flow rate is set to a target value by means of a precision metering valve, and unseeded clean water differential pressure across the filter is recorded. The valve is not adjusted for the remainder of the test, to allow for natural accumulation of differential pressure as plugging or flow decay occurs.

The first challenge liquid is referred to as Seeded General Test Water. It is a seeded (minimum of $10^6$ PFU/ml MS-2) dichlorinated tap water, which is flowed through the test filter on 3 separate challenge cycles at a minimum of 11 void volumes of the system, followed each time by a non-seeded clean water flush cycle, on Day 1. MS-2 is a test organism grown and handled as understood by those skilled in the art.

The second challenge liquid is a seeded (minimum of $10^6$ PFU/ml MS-2) dechlorinated tap water that is spiked with a polyanionic acid, such as humic acid or tannic acid, to a minimum of 10 mg/L Total Organic Carbon, at a pH of 9.0+/−0.2. This second challenge liquid is referred to as Seeded Challenge Water. This liquid is also flowed through the test filter on 3 separate challenge cycles at a minimum of 11 void volumes of the system, followed each time by a non-seeded clean water flush cycle, on Day 2.

Effluent is collected as the 11 th void volume of the filter during all 6 seeded cycles spanning both days, and tested for remaining PFU/ml; the data is converted to the log reduction value (LRV) as is known in the art. In a test that runs to completion of both days without plugging, there are 6 test points of LRV.

By challenging the system (and individual components) with both types of seeded challenge liquid, the point of breakthrough is determined when LRV falls below 4.0.

Alternately, plugging failure is determined at the point when the flow through the filter system decays to 25% of the original value.

The pressure drop across the filter at the beginning of a challenge test is also important, in that a low initial clean water pressure drop (pressure at inlet minus pressure at outlet) is desirable in most service applications. Clean water flow pressure drop (WFdP) is expressed in psid, at a specified gallons-per-minute water flow rate.

A non-destructive indicator of block structure and integrity is the air flow pressure drop (pressure at inlet minus pressure at outlet; which can be useful within a given block product family to compare and screen differences in pore size and/or total porosity. Air flow pressure drop (AFdP) is expressed in inches of water, at a specified liters-per-minute air velocity.

Demonstration System Design considerations: a commercially relevant benchmark of 0.5 GPM as an initial clean water flow rate and a challenge rate is deemed to be acceptable in an 8" nominal length. To model this behavior, a test initial flow rate/challenge rate of 0.31 GPM is chosen for 5"

Example 1

Modification of DE with poly(methyldiallylamine epichlorohydrin) in the absence of a linker was accomplished as follows. An aqueous solution containing a total of 250 mL was prepared by adding: (i) 62.5 g of poly(methyldiallylamine epichlorohydrin) (available from Ciba Specialty Chemicals under the trade name SolfixE; 20% solids by weight), (ii) 62.5 g 5N sodium hydroxide (NaOH) and (iii) sufficient DI water to bring the total volume to 250 mL. One kilogram of DE (sold under the trade name Celite 501 available from World Minerals of Santa Barbara, Calif.) was placed into a one gallon glass jar. The solution of SolfixE was added in 50 mL aliquots with vigorous shaking, and placed on a roller jar mill for 30 minutes after addition of each 50 mL aliquot. After final addition of the 250 mL SolfixE solution, the one gallon container was allowed to mix on the roller jar mill for 1 hour. The resulting fluffy light mixture was then removed from the one gallon jar and placed onto a glass baking dish. The baking dish was then placed in a convection oven at 110° C. overnight. The dry treated DE product was then washed three times with 0.33 gallons of DI water, vacuum filtered through a Buchner funnel (with #415 filter paper) and dried in a convection oven at 110° C. overnight. The ensuing treated DE contained less than 1-3% water by weight.

Example 2A

Modification of the surface of a high purity/pre-processed DE with poly(methyldiallylamine epichlorohydrin) in the absence of a linker was accomplished as follows. Twenty-five kilograms of high purity/pre-processed DE (sold under the trade name Celpure S1000) was placed into a vessel equipped with a plow and a chopper (Model FM-130; available from Littleford Day Inc.) for agitation. A coating solution was prepared by mixing 9.4 kg poly(methyldiallylamine epichlorohydrin) (available from Ciba Specialty Chemicals under the trade name SolfixE) (20% solids), 2.3 kg 5N NaOH, and 25.8 kg of DI water (including the DI water used in making the 5N NaOH solution). The coating solution was sprayed into the vessel while the S1000 DE was agitated. At the same time, the vessel was steam-heated (steam temperature 152±4° C.) to maintain the S1000 DE temperature at about 55° C. under a vacuum of 26±1 inch Hg. After all of the coating solution was sprayed onto the S1000 DE, the steam was maintained until the temperature of the treated S1000 DE was brought up to about 85° C. The heating steam was then terminated and the material was allowed to cool to room temperature.

Extractables were measured using the metanil yellow capacity test. A one liter aqueous solution containing 8 ppm metanil yellow (available from Sigma-Aldrich, Milwaukee, Wis.) buffered at pH=7.0 was prepared. This solution was recirculated, using a persistaltic pump, through a 47 mm cylindrical housing packed with 934AH glass filter material and 0.1 g of the material to be tested for metanil yellow retention. The initial ($Abs_{(init)}$) and final ($Abs_{(final)}$) visible absorbances (at wavelength=430 nm) were measured using a UV-Visible spectrophotometer (LKB Ultrospec II, available from American Instrument Exchange, Haverhill, Mass.; with a 1.0 cm disposable plastic cell). The capacity (mg/g) was calculated as: Capacity=[$Abs_{(init)}$−$Abs_{(final)}$/$Abs_{(init)}$]*8 ppm/wt of test material.

The surface-modified DE prepared according to Example 2A had reduced extractables compared to the prior art method, both after an initial rinse and after multiple wash steps. Moreover, the method of Example 2A has fewer process steps than that of the prior art method.

The chemical stabilities of the surface-modified DE of Example 2A at a pH of 5 and a pH of 9 were measured by the associated charge capacity and the amount of SolfixE (measured in the form of nitrogen) that could be released to the surrounding water. The pH studies were conducting using the following method. Seventy-five grams (75 g) of the surface modified DE to be tested was placed into each of 18 quart glass jars. To each jar was added 750 mL of tap water. Nine (9) of the mixtures in the jars were adjusted to pH=5.0 using sulfuric acid ($H_2SO_4$) and nine of the mixtures in the quart glass jars were adjusted to pH=9.0 using sodium hydroxide (NaOH). Two blank samples were run containing only pH adjusted DI water. Each sample was prepared by vacuum filtration through a #425 filter paper on a Buchner funnel, and further filtered through a 0.2 micron Zetapor™ nylon membrane (available from CUNO, Inc, Meriden Conn.). Stored samples were shaken daily and pH was monitored and adjusted weekly during the duration of the testing. The water was sampled at 20 minutes, 72 hours, 1 week, 2 weeks, 3 weeks 1 month, 2 months, 4 months and 6 months. The results for pH of 5 are provided in Table 1 and for pH of 9 are provided in Table 2, where TKN is the total Kjeldahl nitrogen in the water, and QAE is total quaternary nitrogen in the water. Neither the TKN nor the QAE values change appreciably over the test timeframe of two months, showing that the surface-modified DE was stable over that timeframe.

TABLE 1

| Sample: pH = 5 | Metanil-Yellow (mg/g) | TKN (ppm) | QAE (ppm) |
| --- | --- | --- | --- |
| DI Water Blank | — | ND | ND |
| 20 minutes | 7 | 1.8 | ND |
| 72 hours | 7.3 | 1.9 | ND |
| 1 week | 8.1 | 1.6 | ND |
| 2 weeks | 6.3 | 2.0 | ND |
| 3 weeks | 4.2 | 1.6 | ND |
| 1 month | 5.6 | 1.3 | ND |
| 2 months | 3.5 | 1.7 | ND |
| 4 months | 6.3 | 1.3 | ND |
| 6 months | 12.4 | 1.3 | ND |

TABLE 2

| Sample: pH = 9 | Metanil-Yellow (mg/g) | TKN (ppm) | QAE (ppm) |
| --- | --- | --- | --- |
| DI Water Blank | — | ND | ND |
| 20 minutes | 11 | 1.7 | ND |
| 72 hours | 14 | 1.8 | ND |
| 1 week | 14.3 | 1.8 | ND |
| 2 weeks | 5.2 | 2.1 | ND |
| 3 weeks | 3.7 | 2.1 | ND |
| 1 month | 8.4 | 1.9 | ND |
| 2 months | 3.2 | 1.7 | ND |
| 4 months | 7.3 | 2.0 | <0.30 |
| 6 months | 9.2 | 1.8 | ND |

"ND" = no analyte detected for the sample

Particle size of DE made according to Example 2 ranges from about 20 to about 60 microns, depending on whether agglomeration occurs. Particle size is a function of agglomeration and can be adjusted as desired via manipulation of process parameters such as spray time/nozzle selection/plow speeds/etc.

Example 2B

Modification of the surface of a high purity/pre-processed DE with poly(methyldiallylamine epichlorohydrin) in the absence of a linker was accomplished as follows. In this example, the relative amounts of DE and poly(methyldiallylamine epichlorohydrin) solution were maintained to keep the mixture of these components below its compaction point. In this method, the DE is surface modified using an amount of charge modification resin needed to effect a uniform modification of the surfaces of the DE particles, without excessive resin that would otherwise result in an undesirable initial water extractable species from the formed zone of the present invention. The result is a highly charged cationic surface modified separation media (active media).

Fifty grams of untreated and fully dried (to less than 1-3 weight % water) high purity DE (S1000) was added slowly to 45 grams of an aqueous solution having about 5.5% by weight of poly(methyldiallylamine epichlorohydrin) (SolfixE). The pH was adjusted to about 11 with NaOH. The addition was slow while S1000 was under constant agitation by tumbling the container tilted at an angle for easy dispensing and without the spilling of the content. Optionally, the container could be a closed system to eliminate moisture loss while agitation.

After the addition was completed, the container was further agitated to ensure a uniform liquid distribution among particles. The container was heated to about 100 to 120° C. to complete the reaction. The total nitrogen content due to SolfixE extracted with water at ambient temperature for 24 hours was less than 2.5 ppm. In certain processes, use of excess SolfixE, not in accordance with staying below the compaction point, normally results in having more than 25 ppm total nitrogen extractable; that is 10 times more extractables as compared with maintaining the compaction point.

Example 3

This example describes a typical carbon block formulation, made with components that provide multiple health and aesthetic contaminant reduction in drinking water, but do not claim antimicrobial reduction.

The carbon block was produced according to the Sintered Blocks Procedure using a formulation containing the nominal percentages of components shown in Table 3a:

TABLE 3a

| Component | % in blend |
|---|---|
| Binder PMX2 (small sphere) UHMW PE - GUR 4150-3 | 14.5 |
| Binder PMX3 (large convoluted) UHMW PE - GUR 2122 | 30.5 |
| Coarse carbon CR, 80 × 325 Acid washed coconut carbon | 27 |
| Fine carbon GX203 Fine shell Coconut VOC | 16 |
| ATS Lead removal Zeolite | 12 |

The mold used for the Example 3 blocks was an engine-block style mold with four cavities, nominally 10" length, in a production environment. An engine block mold was machined from a solid block of metal (in this case aluminum). The weight of the engine block provided significant damping of the vibration table during filling. The column of powder was compressed by a shallow indent in the top plate, after filling and vibration was complete. The block was heated using pressurized steam as the heat source. Cooling was effected by pumping water through the steam channels after heating, until the system was at approximately room temperature. Blocks were ejected and sent for further processing. The blocks were trimmed to a final geometry of nominally 3" OD×1.5" ID×6" height, and fitted with adaptors (threaded top, solid bottom) for an AP200 filter housing (available from CUNO, Inc. of Meriden, Conn.), then were tested for AFdP (air flow pressure drop) and WFdP (water flow pressure drop). Physical characteristics of block weight and length were measured and the averages of these measurements for 3 representative blocks are provided in Table 3b:

TABLE 3b

| | |
|---|---|
| O.D., in. | 3.0 |
| I.D., in. | 1.5 |
| Trimmed length, in. | 6.10 |
| Weight, g | 267.13 |
| Weight per unit length, g/in. | 43.79 |
| AFdP @ 15 LPM, in. $H_2O$ | 3.02 |
| WFdP @ 0.31 GPM, psi | 5.43 |
| WFdP @ 0.5 GPM, psi | 11.00 |
| Normalized WFdP (linear) @ 0.5 GPM, (dP*in.) | 67.1 |

Example 4

This example describes a typical carbon block formulation, made with components that provide multiple health and aesthetic contaminant reduction in drinking water, but do not claim antimicrobial reduction. This carbon block as a sleeve does not effectively reduce virus in the test conditions.

The carbon block was produced according to the Sintered Blocks Procedure using a formulation containing the nominal percentages of components shown in Table 3a for Example 3.

The mold used for the Example 4 blocks was the same as that used in Example 3. For Example 4, however, equipment and process variables (such as vibration and fill time) were changed, and raw material batches were rotated, to effect a change in the resulting blocks. As such, a combined variation of process and materials, on a constant formulation result in different physical characteristics of the blocks. The decrease in length-normalized WFdP of Example 4 compared to Example 3 indicates that Example 4 blocks have a lower density structure than the Example 3 blocks. Physical characteristics of block weight and length were measured for 3 representative blocks, which are provided in Table 4b:

TABLE 4b

| | Ex. 4-A | Ex. 4-B | Ex. 4-C | Average |
|---|---|---|---|---|
| O.D., in. | 3.0 | 3.0 | 3.0 | 3.0 |
| I.D., in. | 1.5 | 1.5 | 1.5 | 1.5 |
| Trimmed length, in. | 5.0 | 5.0 | 5.0 | 5.0 |
| AFdP @ 15 LPM, in. $H_2O$ | 1.50 | 1.50 | 1.63 | 1.54 |
| WFdP @ 0.31 GPM, psi | 3.10 | 2.70 | 3.50 | 3.10 |
| WFdP @ 0.5 GPM, psi | 6.4 | 5.7 | 7.8 | 6.63 |
| Normalized WFdP (linear) @ 0.5 GPM, dP*in | 32.0 | 28.5 | 39.0 | 33.2 |

The blocks were tested according to the rapid 2-day Microbial Challenge described above, using humic acid as the TOC adjustment on Day 2. The 500 cc void volume MS-2 phage challenge testing results are provided in Tables 4c (Day 1) and 4d (Day 2); at a preset challenge flow rate of 0.31 GPM, where ND means not detected.

TABLE 4c

Microbiological Analysis of Filter Devices Challenged With Seeded General Test Water (Day 1)

| Cycle | Inlet (PFU/mL) | Ex. 4-A (PFU/mL) | LRV | Ex. 4-B (PFU/mL) | LRV | Ex. 4-C (PFU/mL) | LRV |
|---|---|---|---|---|---|---|---|
| 2 | 2.0E+0 | ND | — | ND | — | ND | — |
| 3 | 5.3E+6 | 5.8E+3 | 3.0 | 4.5E+4 | 2.1 | 6.3E+4 | 1.9 |
| 5 | 7.5E+6 | 2.0E+5 | 1.6 | 1.8E+4 | 2.6 | 5.7E+4 | 2.1 |
| 7 | 9.1E+6 | 1.8E+5 | 1.7 | 2.6E+4 | 2.5 | 6.9E+4 | 2.1 |
| 8 | 8.8E+3 | 5.5E+3 | — | 2.6E+2 | — | 2.9E+3 | — |

TABLE 4d

Microbiological Analysis of Filter Devices Challenged With Seeded Challenge Test Water (Day 2)

| Cycle | Inlet (PFU/mL) | Ex. 4-A (PFU/mL) | LRV | Ex. 4-B (PFU/mL) | LRV | Ex. 4-C (PFU/mL) | LRV |
|---|---|---|---|---|---|---|---|
| S | 1.0E+4 | 2.3E+3 | — | 2.0E+0 | — | 2.1E+2 | — |
| 2 | 4.8E+6 | 4.0E+5 | 1.1 | 8.8E+4 | 1.7 | 2.0E+5 | 1.4 |
| 4 | 5.0E+6 | 2.1E+6 | 0.4 | 1.5E+5 | 1.5 | 3.8E+6 | 0.1 |
| 6 | 4.9E+6 | 2.8E+6 | 0.2 | 6.3E+6 | 0.1 | 5.0E+6 | 0.1 |
| 7 | 9.3E+2 | 5.4E+4 | — | 5.6E+4 | — | 6.1E+4 | — |

When determining antimicrobial reduction potential, an acceptable challenge for any cycle must demonstrate no less than 4.0 LRV. As such none of these blocks passed the acceptance criteria at any challenge point; the blocks cannot be considered reductive to MS-2. However, in no case did the flow rate decay significantly (less than 25% of initial clean water preset flow rate).

The block formulation of Examples 3 and 4 is an effective formulation for chlorine, taste and odor reduction, etc., but is not effective for viral reduction. Any substantial phage reduction capability in a 2-zone system containing this carbon block will therefore be attributable to the other zone.

Example 5

This example describes a typical carbon block formulation, made with components that provide multiple health and aesthetic contaminant reduction in drinking water, but do not claim antimicrobial reduction.

The carbon block was produced according to the Sintered Blocks Procedure using a formulation containing the nominal percentages of components shown in Table 5a:

TABLE 5a

| Component | % in blend |
|---|---|
| Binder PMX1 (small convoluted) UHMW PE - GUR 2126 | 37 |
| Binder PMX2 (small sphere) UHMW PE - GUR 4150-3 | 17 |
| Coarse carbon CR, 80 × 325 Acid washed coconut carbon | 7 |
| Water washed fine shell coconut carbon | 29 |
| ATS | 10 |
| Lead removal Zeolite | |

The mold used for the Example 5 blocks included individual tubes of aluminum, fashioned from aluminum pipe stock cut to length, in a pilot laboratory environment. The cut tubes were nominally 8" in length, then mated with individual bottom plates, mandrels, and top plates. A different vibration table was used compared to Examples 3 and 4, adapted to the tubes. After vibration filling of the tubes, the tubes were relocated to a station where a pneumatic cylinder was mounted directly above each individual tube, with a piston facing the tube. A washer was placed on the top of the column of powder. The washer was sized to provide a slip fit between the ID of the tube, and the OD of the mandrel. The piston was activated to press the washer down into the tube. By this action, the washer displaced and compressed the powder slightly; and provided a mechanical indexing of the location of the mandrel relative to the side wall of the aluminum tube; which also served to prevent relative motion between the tube and the mandrel. This way, when the top plate was fastened to the mold, the mandrel was less likely to disturb the packed powder. The completed assemblies of bottom plates with mandrel, tube shell, packed powder, washer, and top plate were placed in a forced-draft oven for heating. Cooling was effected by removing molds from the oven and placing them on a cooling rack in ambient air, with a fan blowing on the tubes, until the tubes reached approximately room temperature. Physical characteristics of block weight and length were measured and the averages of these measurements for 3 representative blocks are provided in Table 5b:

TABLE 5b

| | |
|---|---|
| O.D., in. | 2.9 |
| I.D., in. | 1.5 |
| Trimmed length, in. | 5.92 |
| Weight, g | 304.70 |
| Weight per unit length, g/in. | 51.51 |
| AFdP @ 15 LPM, in. $H_2O$ | 11.05 |
| WFdP @ 0.31 GPM, psi | 7.74 |
| WFdP @ 0.5 GPM, psi | 12.63 |
| Normalized WFdP (linear) @ 0.5 GPM, dP*in | 74.7 |

The block formulation of Example 5 is an effective formulation for chlorine, taste and odor reduction, etc., and with its nominally tighter pore structure compared to Examples 3 and 4, has been demonstrated to be effective for cyst reduction. Examples 3 and 4 are not suitable for cyst reduction. The block of Example 5 is suitable for use in a 2-zone system.

Example 6

Comparative

This example measured the viral reduction capability of an unmodified DE block formulation, having two principal components: DE and UHMW PE.

The block was produced according to the Sintered Blocks Procedure using a formulation containing the nominal percentages of components shown in Table 6a:

TABLE 6a

| Component | % in blend |
|---|---|
| Binder PMX1 (small convoluted) UHMW PE - GUR 2126 | 41.6 |
| Binder PMX2 (small sphere) UHMW PE - GUR 4150-3 | 8.3 |
| Celite 501 Natural Diatomaceous Earth | 50 |

The mold for the Example 6 blocks was formed from steel, designed to deliver nominally 8" tall blocks, 1.5" OD and 0.375" ID. A steam heat source was used. Physical characteristics of block weight and length were measured for 3 representative full height blocks, adapted with suitable end caps, which are provided in Table 6b:

TABLE 6b

|  | Ex. 6-A | Ex. 6-B | Ex. 6-C | Average |
|---|---|---|---|---|
| O.D., in. | 1.4 | 1.4 | 1.4 | 1.4 |
| I.D., in. | 0.375 | 0.375 | 0.375 | 0.375 |
| Full length, in. | 8.0 | 8.0 | 8.0 | 8.0 |
| Full Weight, g | 80.6 | 80.8 | 81.3 | 80.9 |
| Weight per unit length, g/in. | 10.1 | 10.1 | 10.1 | 10.1 |
| AFdP @ 15 LPM, in. $H_2O$ | 5.77 | 5.74 | 5.70 | 5.74 |
| WFdP @ 0.5 GPM, psi | 10.3 | 10.5 | 10.8 | 10.5 |
| Normalized WFdP (linear) @ 0.5 GPM, dP*in | 82.5 | 84.2 | 86.5 | 84.4 |

The blocks were tested according to the rapid 2-day Microbial Challenge described above, using humic acid as the TOC adjustment on Day 2. Due to the more efficient standard refrigerator system cartridge and housing design, the void volume was reduced to 180 cc. The 180 cc void volume MS-2 phage challenge testing results are provided in Tables 6c (Day 1) and 6d (Day 2); at a preset challenge flow rate of 0.5 GPM, where ND means not detected.

TABLE 6c

Microbiological Analysis of Filter Devices Challenged With Seeded General Test Water (Day 1)

| Cycle | Inlet (PFU/mL) | Ex. 6-A (PFU/mL) | LRV | Ex. 6-B (PFU/mL) | LRV | Ex. 6-C (PFU/mL) | LRV |
|---|---|---|---|---|---|---|---|
| 2 | 4.0E+0 | ND | — | ND | — | ND | — |
| 3 | 9.2E+5 | >E+5 | <1 | >E+5 | <1 | >E+5 | <1 |
| 5 | 1.2E+6 | >E+5 | <1 | >E+5 | <1 | >E+5 | <1 |
| 7 | 4.5E+6 | >E+5 | <1 | >E+5 | <1 | >E+5 | <1 |
| 8 | 2.6E+4 | 2.8E+4 | — | * | — | 1.1E+4 | — |

*no data obtained.

TABLE 6d

Microbiological Analysis of Filter Devices Challenged With Seeded General Test Water (Day 2)

| Cycle | Inlet (PFU/mL) | Ex. 6-A (PFU/mL) | LRV | Ex. 6-B (PFU/mL) | LRV | Ex. 6-C (PFU/mL) | LRV |
|---|---|---|---|---|---|---|---|
| S | 5.6E+3 | 1.7E+2 | — | 5.1E+1 | — | 6.8E+1 | — |
| 2 | 3.0E+6 | >E+5 | <1 | >E+5 | <1 | >E+5 | <1 |
| 4 | 4.1E+6 | >E+5 | <1 | >E+5 | <1 | >E+5 | <1 |
| 6 | 2.5E+6 | >E+5 | <1 | >E+5 | <1 | >E+5 | <1 |
| 7 | 1.8E+4 | 2.4E+4 | — | 2.7E+4 | — | 2.1E+4 | — |

There was no measurable reduction of the MS-2 phage with the comparative blocks of Example 6. At the reduced void volume and full 8" length tested in Example 6, there was no plugging event recorded in the humic acid environment.

Example 7

This example measured the viral reduction capability of a modified DE block formulation, having two principal components: the modified high purity DE made according to Example 2A and UHMW PE.

The block was produced according to the Sintered Blocks Procedure using a formulation containing the nominal percentages of components shown in Table 7a:

TABLE 7a

| Component | % in blend |
|---|---|
| Binder PMX1 (small convoluted) UHMW PE - GUR 2126 | 41.7 |
| Binder PMX2 (small sphere) UHMW PE - GUR 4150-3 | 8.3 |
| Modified Pre-processed Diatomaceous Earth of Example 2A | 50 |

The mold for the Example 7 blocks was the same as that used in Example 5, having dimensions designed to deliver nominally 8" tall blocks, 1.5" OD and 0.375" ID. Vibration only was used only for compaction of material. That is, unlike the blocks formed in Example 5, there was no top compression or washer insertion. The blocks were trimmed to 5.0" length, adapted for insertion into an AP200 test housing, and fitted with plastic inserts to limit the void volume of the combination housing and block to 180 cc. Physical characteristics of block weight and length were measured for 3 representative full length blocks, adapted with suitable end caps, which are provided in Table 7b:

TABLE 7b

|  | Ex. 7-A | Ex. 7-B | Ex. 7-C | Average |
|---|---|---|---|---|
| O.D., in. | 1.5 | 1.5 | 1.5 | 1.5 |
| I.D., in. | 0.375 | 0.375 | 0.375 | 0.375 |
| Full Length, in. | 8.4 | 8.6 | 8.3 | 8.4 |
| Full Weight, g | 99.9 | 99.4 | 93.6 | 97.6 |
| Weight per unit length, g/in. | 11.9 | 11.6 | 11.2 | 11.6 |
| AFdP @ 15 LPM, in. $H_2O$ | 17.16 | 11.18 | 10.31 | 12.88 |
| WFdP @ 0.5 GPM, psi | 34.9 | 24.4 | 25.0 | 28.10 |
| Normalized WFdP, dP*in | 174.5 | 122.0 | 125.0 | 140.5 |

The blocks were tested according to the rapid 2-day Microbial Challenge described above, using tannic acid as the TOC adjustment on Day 2. The 180 cc void volume MS-2 phage challenge testing results are provided in Tables 7c (Day 1) and 7d (Day 2); at a preset challenge flow rate of 0.31 GPM, where ND means not detected, FD means flow decay, and "TE" means no sample was taken.

TABLE 7c

Microbiological Analysis of Filter Devices Challenged With Seeded General Test Water (Day 1)

| Cycle | Inlet (PFU/mL) | Ex. 7-A (PFU/mL) | LRV | Ex. 7-B (PFU/mL) | LRV | Ex. 7-C (PFU/mL) | LRV |
|---|---|---|---|---|---|---|---|
| 2 | ND | ND | — | ND | — | ND | — |
| 3 | 3.4E+6 | ND | 6.5 | 2.4E+3 | 3.2 | 3.1E+1 | 5.0 |

TABLE 7c-continued

Microbiological Analysis of Filter Devices Challenged
With Seeded General Test Water (Day 1)

| Cycle | Inlet (PFU/mL) | Ex. 7-A (PFU/mL) | LRV | Ex. 7-B (PFU/mL) | LRV | Ex. 7-C (PFU/mL) | LRV |
|---|---|---|---|---|---|---|---|
| 5 | 2.7E+6 | ND | 6.4 | 8.0E+3 | 2.5 | 2.2E+1 | 5.1 |
| 7 | 3.0E+6 | ND | 6.5 | 8.9E+3 | 2.5 | 3.6E+1 | 4.9 |
| 8 | TE | 1.0E+0 | — | TE | — | ND | — |

TABLE 7d

Microbiological Analysis of Filter Devices Challenged
With Seeded Challenge Test Water (Day 2)

| Cycle | Inlet (PFU/mL) | Ex. 7-A (PFU/mL) | LRV | Ex. 7-B (PFU/mL) | LRV | Ex. 7-C (PFU/mL) | LRV |
|---|---|---|---|---|---|---|---|
| S | 2.8E+2 | ND | — | ND | — | ND | — |
| 2 | 2.5E+6 | ND | 6.4 | 1.6E+4 | 2.2 | 2.8E+3 | 3.0 |
| 4 | 2.2E+6 | 1.0E+0 | 6.3 | 1.4E+4 | 2.2 | 5.4E+3 | 2.6 |
| 6 | 2.0E+6 | FD | FD | FD | FD | FD | FD |
| 7 | | FD | FD | FD | FD | FD | FD |

After the challenge testing, the blocks were removed from the housing, and broken into cross sections at various points along the length of the block. Cracks were found in Ex. 7-B, and smaller cracks were found in Ex. 7-C; mostly internal to the matrix (not visible at a surface) and penetrating through the matrix to the ID of the block. The presence of cracking in the structure appears to have compromised the antimicrobial performance. In addition, in the presence of tannic acid, early flow decay (all blocks were plugged prior to or during Day 2 cycle 6) inhibited a complete analysis of the antimicrobial capacity. No significant cracking was found in Ex. 7-A. The penetration of the block by tannic acid was visible as a color ring around the OD of the block, without a significant penetration of color to the center of the block.

Example 8

This example measured the viral reduction capability of a modified DE block formulation, having two principal components: the modified high purity DE made according to Example 2A and UHMW PE.

The block was produced according to the Sintered Blocks Procedure using a formulation containing the nominal percentages of components used in Example 7.

The mold for the Example 8 blocks was the same as that used in Example 7, with the addition of stiffer central mandrels to limit the effect of differential motion between tube and mandrel during vibration. The blocks were trimmed to 5.0" length, adapted for insertion into an AP200 test housing, and fitted with plastic inserts to limit the void volume of the combination housing and block to 180 cc. Physical characteristics of block weight and length were measured for 3 representative full height blocks, adapted with suitable end caps, which are provided in Table 8a:

TABLE 8a

| | Ex. 8-A | Ex. 8-B | Ex. 8-C | Average |
|---|---|---|---|---|
| O.D., in. | 1.5 | 1.5 | 1.5 | 1.5 |
| I.D., in. | 0.375 | 0.375 | 0.375 | 0.375 |
| Full Length, in. | 8.4 | 8.5 | 8.5 | 8.4 |
| Full Weight, g | 93.5 | 98.0 | 93.8 | 95.1 |
| Weight per unit length, g/in. | 11.2 | 11.6 | 11.1 | 11.3 |
| AFdP @ 15 LPM, in. H$_2$O | 13.12 | 13.51 | 11.62 | 12.75 |
| WFdP @ 0.5 GPM, psi | 31.6 | 29.6 | 28.1 | 29.77 |
| Normalized WFdP, dP*in | 158.0 | 148.0 | 140.5 | 148.8 |

The blocks were tested according to the rapid 2-day Microbial Challenge described above, using tannic acid as the TOC adjustment on Day 2. The 180 cc void volume MS-2 phage challenge testing results are provided in Tables 8b (Day 1) and 8c (Day 2); at a preset challenge flow rate of 0.31 GPM, where ND means not detected, FD means flow decay, and "-" means no sample taken.

TABLE 8b

Microbiological Analysis of Filter Devices Challenged
With Seeded General Test Water (Day 1)

| Cycle | Inlet (PFU/mL) | Ex. 8-A (PFU/mL) | LRV | Ex. 8-B (PFU/mL) | LRV | Ex. 8-C (PFU/mL) | LRV |
|---|---|---|---|---|---|---|---|
| 2 | 1.0E+1 | ND | — | ND | — | ND | — |
| 3 | 3.1E+6 | ND | 6.5 | ND | 6.5 | ND | 6.5 |
| 5 | 3.9E+6 | ND | 6.6 | ND | 6.6 | ND | 6.6 |
| 7 | 4.3E+6 | ND | 6.6 | ND | 6.6 | ND | 6.6 |
| 8 | 2.9E+2 | ND | — | ND | — | ND | — |

TABLE 8c

Microbiological Analysis of Filter Devices Challenged
With Seeded Challenge Test Water (Day 2)

| Cycle | Inlet (PFU/mL) | Ex. 8-A (PFU/mL) | LRV | Ex. 8-B (PFU/mL) | LRV | Ex. 8-C (PFU/mL) | LRV |
|---|---|---|---|---|---|---|---|
| S | 1.7E+4 | ND | — | ND | — | ND | — |
| 2 | 3.4E+6 | ND | 6.5 | ND | 6.5 | ND | 6.5 |
| 4 | 2.1E+6 | ND | 6.3 | ND | 6.3 | ND | 6.3 |
| 6 | 2.6E+6 | ND | 6.4 | ND | 6.4 | ND | 6.4 |
| 7 | 5.3E+1 | ND | — | ND | — | ND | — |

The blocks of Example 8 did not plug in the tannic acid environment, nor did they exhibit early breakthrough of MS-2 phage. There was no change in the formulation; but the laboratory process and apparatus used to produce these blocks were changed. The blocks of Example 8, therefore, have effective antimicrobial functionality by viral (phage) reduction as a stand-alone block in a polyanionic acid environment. In contrast, the similar stand alone article of Example 6 without the cationic surface modification to the DE is not functional. Later testing with tannic acid demonstrated inconsistent plugging behavior of blocks, likely due to variability among tannic acid batches. For certification testing in the State of California, however, humic acid is the preferred species.

Example 9

This example measured the viral reduction capability of a modified DE block formulation, having two principal components: the modified high purity DE made according to Example 2B and UHMW PE; and one minor component, which was a relatively large carbon particle (nominally 100 um d50 steam activated coconut shell carbon) additive at a 5% level. The addition of the minor component carbon particle enhanced the structural characteristics of the block. As in examples 7 and 8, the high purity Celpure DE was chosen for the starting material.

The block was produced according to the Sintered Blocks Procedure using a formulation containing the nominal percentages of components shown in Table 9a:

TABLE 9a

| Component | % in blend |
|---|---|
| Binder PMX1 (small convoluted) UHMW PE - GUR 2126 | 20.8 |
| Binder PMX2 (small sphere) UHMW PE - GUR 4150-3 | 4.2 |
| Modified Pre-processed Diatomaceous Earth of Example 2B | 70 |
| Steam activated coconut shell carbon (nominally 100 um d50) | 5 |

The mold for the Example 9 blocks was the same as that used in Example 5. For Example 9, however, the process included the use of top compression of the vibrated packed powder, plus washers to stabilize the powder and motion of the mandrel relative to the tube wall. The mold was filled using vigorous vibration to the point of being nominally full. A washer was placed over the vibrated powder and was a slip fit to the mold ID and the mandrel OD. The washer was gently pressed into the powder and into the mold, such that it was in contact with both the inner wall of the mold, and the mandrel. Care was taken not to move the mandrel relative to the tube wall, creating a disturbance in the packing of the powder. The assembly (powder, mold, mandrel, and washer) was then carefully positioned beneath a plunger mounted on an air cylinder. The plunger OD was slightly smaller than the ID of the mold, and contained a guide hole capable of engaging the mandrel; the guide hole was slightly larger than the OD of the mandrel. The air cylinder was engaged, and the plunger was allowed to drive the washer further into the mold cavity, to either an endpoint pressure or an endpoint displacement, as desired. After heating, sintering, cooling, and block ejection, the washer was removed from the top of the block.

The blocks were trimmed to 5.0" length, adapted for insertion into an AP200 test housing, and fitted with plastic inserts to limit the void volume of the combination housing and block to 180 cc. Physical characteristics of block weight and length were measured for 3 representative full height blocks, adapted with suitable end caps, which are provided in Table 7b:

TABLE 9b

|  | Ex. 9-A | Ex. 9-B | Ex. 9-C | Average |
|---|---|---|---|---|
| O.D., in. | 1.5 | 1.5 | 1.5 | 1.5 |
| I.D., in. | 0.375 | 0.375 | 0.375 | 0.375 |
| Full Length, in. | 7.8 | 7.5 | 7.5 | 7.6 |
| Full Weight, g | 100.8 | 96.9 | 96.3 | 98.0 |
| Weight per unit length, g/in. | 13.0 | 12.9 | 12.8 | 12.9 |
| AFdP @ 15 LPM, in. $H_2O$ | 18.98 | 15.85 | 16.35 | 17.06 |
| WFdP @ 0.31 GPM, psi | 19.4 | 18.2 | 18.7 | 18.8 |

TABLE 9b-continued

|  | Ex. 9-A | Ex. 9-B | Ex. 9-C | Average |
|---|---|---|---|---|
| WFdP @ 0.5 GPM, psi | 35.2 | 31.8 | 31.3 | 32.77 |
| Normalized WFdP, dP*in | 176.0 | 159.0 | 156.5 | 163.8 |

The full length differences between Example 9 and Examples 6-8 are attributable to the mild compression used in the Example 9 block preparation. The blocks of Example 9 have a modest increase in block density, and only a small increase in normalized water flow pressure drop, when compared to non-compressed blocks such as in Examples 7 and 8.

The blocks were tested according to the rapid 2-day Microbial Challenge described above, using humic acid as the TOC adjustment on Day 2. The MS-2 phage challenge testing was conducted at an equivalent of 500 ml void volume despite the void volume being 180 cc. This was intended to increase the microbiological load and humic acid load on the blocks of the present example. The MS-2 phage challenge testing results are provided in Tables 9c (Day 1) and 9d (Day 2); at a preset challenge flow rate of 0.31 GPM, where ND means not detected and FD means flow decay.

TABLE 9c

Microbiological Analysis of Filter Devices Challenged With Seeded General Test Water (Day 1)

| Cycle | Inlet (PFU/mL) | Ex. 9-A | | Ex. 9-B | | Ex. 9-C | |
|---|---|---|---|---|---|---|---|
|  |  | (PFU/mL) | LRV | (PFU/mL) | LRV | (PFU/mL) | LRV |
| 2 | 2.0E+0 | ND | — | ND | — | ND | — |
| 3 | 5.0E+6 | ND | 6.7 | ND | 6.7 | ND | 4.0 |
| 5 | 5.1E+6 | ND | 6.7 | 1.0E+0 | 6.7 | ND | 3.9 |
| 7 | 5.4E+6 | ND | 6.7 | 6.0E+0 | 6.0 | ND | 3.7 |
| 8 | 4.2E+3 | ND | — | 1.6E+1 | — | 1.5E+1 | — |

TABLE 9d

Microbiological Analysis of Filter Devices Challenged With Seeded Challenge Test Water (Day 2)

| Cycle | Inlet (PFU/mL) | Ex. 9-A | | Ex. 9-B | | Ex. 9-C | |
|---|---|---|---|---|---|---|---|
|  |  | (PFU/mL) | LRV | (PFU/mL) | LRV | (PFU/mL) | LRV |
| S | >10⁵ | 1.0E+0 | — | 4.0E+0 | — | 1.6E+1 | — |
| 2 | 3.9E+6 | ND | 6.6 | ND | 6.6 | 4.8E+2 | 3.9 |
| 4 | 4.8E+6 | FD | FD | FD | FD | FD | FD |
| 6 | FD | FD | FD | FD | FD | FD | FD |
| 7 | FD | FD | — | FD | — | FD | — |

As can be seen from the data for blocks 9-A and 9-B, the full capacity of the block formulation to MS-2 cannot be evaluated due to early flow decay and plugging of the block. Also notable is the more rapid plugging, where flow decay was severe enough to prevent the blocks from being tested on Day 2 cycle 4; this may be attributed to the higher challenge volumes (500 ml void volume challenge) when compared to previous examples. Block 9-C may have suffered from a structural deficiency; i.e. a small and constant bypass of unfiltered fluid that can be attributed to a pinhole, small crack or end cap leak, which was apparent from the beginning of the test.

Example 10

This example measured the viral reduction capability of a zoned filtration system configured in an annular concentric arrangement of 2 zones. For Example 10, a first zone of carbon block (according to Example 3) was added to protect an anti-microbial core zone (according to Example 9).

A series of Example 3 carbon blocks were produced, at nominally 10" length. A series of Example 9 blocks were produced, at approximately 7.5" length. The Example 9 blocks were inserted into the ID of the Example 3 blocks. Both were trimmed together at one end on a mitering saw, to create a single face, to which a bottom end cap was glued. The combination was trimmed again on the mitering saw to a block body length of 5 inches, and the threaded top end cap was fitted and glued. The combination (hybrid) annular concentric discrete zone filter was tested for physical characteristics; shown in Table 10a:

TABLE 10a

| | Ex. 10-A | Ex. 10-B | Ex. 10-C | Average |
|---|---|---|---|---|
| Anti-microbial Core only | | | | |
| O.D., in. | 1.5 | 1.5 | 1.5 | 1.5 |
| I.D., in. | 0.375 | 0.375 | 0.375 | 0.375 |
| Full length, in. | 7.7 | 7.6 | 7.5 | 7.6 |
| Full Weight, g | 98.4 | 95.2 | 92.9 | 95.5 |
| Combined anti-microbial core and carbon block outer zone | | | | |
| AFdP @ l5 LPM, in. $H_2O$ | 16.56 | 16.70 | 16.86 | 16.71 |
| WFdP @ 0.31 GPM, psi | 17.8 | 17.6 | 19.0 | 18.13 |
| WFdP @ 0.5 GPM, psi | 31.2 | 30.1 | 31.4 | 30.90 |
| Normalized WFdP, dP*in | 156.0 | 150.5 | 157.0 | 154.5 |

The annular concentric discrete zone filter was inserted into an AP200 test housing, with no inserts to limit the void volume of the combination housing and block. The blocks were tested according to the rapid 2-day Microbial Challenge described above, using humic acid as the TOC adjustment on Day 2. The 500 cc void volume MS-2 phage challenge testing results are provided in Tables 10b (Day 1) and 10c (Day 2); at a preset challenge flow rate of 0.31 GPM, where ND means not detected and FD means flow decay.

TABLE 10b

Microbiological Analysis of Filter Devices Challenged With Seeded General Test Water (Day 1)

| | Inlet | Ex. 10-A | | Ex. 10-B | | Ex. 10-C | |
|---|---|---|---|---|---|---|---|
| Cycle | (PFU/mL) | (PFU/mL) | LRV | (PFU/mL) | LRV | (PFU/mL) | LRV |
| 2 | ND | 7.00E+00 | — | ND | — | ND | — |
| 3 | 6.70E+06 | ND | 6.8 | ND | 6.8 | ND | 6.8 |
| 5 | 4.40E+06 | ND | 6.6 | ND | 6.6 | 5.00E+00 | 5.9 |
| 7 | 5.60E+06 | ND | 6.7 | ND | 6.7 | ND | 6.7 |
| 8 | 2.10E+02 | ND | — | ND | — | ND | — |

TABLE 10c

Microbiological Analysis of Filter Devices Challenged With Seeded Challenge Test Water (Day 2)

| | Inlet | Ex. 10-A | | Ex. 10-B | | Ex. 10-C | |
|---|---|---|---|---|---|---|---|
| Cycle | (PFU/mL) | (PFU/mL) | LRV | (PFU/mL) | LRV | (PFU/mL) | LRV |
| S | 2.70E+01 | ND | — | ND | — | ND | — |
| 2 | 5.70E+06 | ND | 6.8 | ND | 6.8 | ND | 6.8 |
| 4 | 3.50E+06 | ND | 6.5 | ND | 6.5 | ND | 6.5 |
| 6 | 2.70E+06 | 3.00E+00 | 6.0 | ND | 6.4 | 2.00E+00 | 6.1 |
| 7 | 8.00E+02 | ND | — | ND | — | ND | — |

The carbon block according to Example 3 protected the antimicrobial core according to Example 9 from the premature clogging by a colloidal portion of the polyanionic acid contaminant, additionally allowing the test to proceed to the end point of service life (after the specified volume of seeded challenge test water had passed through the system), without an unacceptable flow decay. Additionally, the anti-microbial core zone effectively adsorbed both the total MS-2 challenge and the dissolved portion of the polyanionic acid. The effective MS-2 adsorption was demonstrated by an LRV rating of greater than 4.0 at each tested point in the challenge cycle.

Example 11

Carbon blocks for use in zoned filtration systems were produced according to the Sintered Blocks Procedure using a formulation containing the nominal percentages of components shown in Table 11a:

TABLE 11a

| Component | % in blend |
|---|---|
| Binder PMX1 (small convoluted) UHMW PE - GUR 2126 | 20 |
| Binder PMX2 (small sphere) UHMW PE - GUR 4150-3 | 30 |
| Coarse carbon CR, 80 × 325 | 50 |

The mold used for the Example 11 carbon blocks was the same as for Example 3.

Example 12

Blocks were produced according to the Sintered Blocks Procedure using a formulation containing the nominal percentages of components shown in Table 12a:

TABLE 12a

| Component | % in blend |
|---|---|
| Binder PMX1 (small convoluted) UHMW PE - GUR 2126 | 35 |
| Modified Pre-processed Diatomaceous Earth of Example 2B | 60 |
| Steam activated coconut shell carbon (nominally 100 um d50) | 5 |

The mold used for the Example 12 blocks was the same as for Example 5.

Example 13

Blocks were produced according to the Sintered Blocks Procedure using a formulation containing the nominal percentages of components shown in Table 13a:

TABLE 13a

| Component | % in blend |
|---|---|
| Binder PMX1 (small convoluted) UHMW PE - GUR 2126 | 29.2 |
| Binder PMX2 (small sphere) UHMW PE - GUR 4150-3 | 5.8 |
| Modified Pre-processed Diatomaceous Earth of Example 2B | 60 |
| Steam activated coconut shell carbon (nominally 100 um d50) | 5 |

The mold used for the Example 13 blocks was the same as for Example 5.

Example 14

A series of hybrid examples were prepared, using different concentrations of active media in the anti-microbial zone, different geometries (variations of ID and OD) of both the anti-microbial zone and the carbon block zone, and the resultant physical characteristics of the hybrids. Also included are the microbiological test results of each. Reference to "% modified DE" means the percent of DE in the core that was prepared according to Example 2A. Reference to "sieved" means that modified DE was sieved through a 400 micron sieve prior to the preparation of the core block. Reference to "Hybrid Q" means the flow rate of filter hybrid in gallons/minute. Reference to media means the total of binders and active materials used to make the core. Empty bed contact time in seconds is referred to as "EBCT" in Table 14a.

Hybrid Example Combinations and Performance Characteristics

TABLE 14a

| | 14-A | 14-B | 14-C | 14-D | 14-E | 14-F |
|---|---|---|---|---|---|---|
| Sleeve | Example 3 | Example 3 | Example 3 | Example 11 | Example 11 | Example 11 |
| Antimicrobial Core | Example 9 | Example 9 | Example 12 | Example 12 | Example 12 | Example 12 |
| % modified DE | 70 | 70 | 60 | 60 | 60 | 60 |
| | No sieve | Sieved | Sieved | Sieved | Sieved | Sieved |
| AFdP @ 15 LPM | 16.38 | 24.17 | 18.87 | 15.78 | 15.81 | 15.81 |
| WFdP @ 0.5 GPM | 30.90 | 39.03 | 28.97 | 25.70 | 24.43 | 23.76 |
| Normalized WFdP to 8" block | 19.313 | 24.394 | 18.106 | 16.063 | 15.269 | 14.850 |
| Core Block Weight, g | 94.71 | 103.23 | 98.03 | 92.20 | 87.04 | 87.04 |
| Core Block Length, in. | 7.556 | 7.50 | 7.58 | 7.38 | 7.05 | 7.05 |
| Normalized Core wt, g/in | 12.53 | 13.77 | 12.93 | 12.50 | 12.34 | 12.34 |
| LRV Day2 avg. | 6.49 | 5.38 | 5.18 | 5.64 | 6.30 | 6.30 |
| LRV D2C6 avg. | 6.2 | 4.63 | 2.9 | 2.6 | 6.70 | 6.70 |
| Hybrid Q gal/min | 0.31 | 0.31 | 0.31 | 0.31 | 0.31 | 0.31 |
| Core Length, in. | 5.00 | 5.00 | 5.00 | 5.00 | 5.00 | 5.00 |
| Core I.D., in. | 0.375 | 0.375 | 0.375 | 0.375 | 0.375 | 0.375 |
| Core O.D., in. | 1.5 | 1.5 | 1.5 | 1.5 | 1.5 | 1.5 |
| Core Volume, in$^3$ | 8.28 | 8.28 | 8.28 | 8.28 | 8.28 | 8.28 |
| EBCT Sec | 6.9 | 6.9 | 6.9 | 6.9 | 6.9 | 6.9 |

TABLE 14b

| | 0.75" ID | |
|---|---|---|
| | 14-G | 14-H |
| Sleeve | Example 11 | Example 3 |
| Antimicrobial Core | Example 13 Sieved | Example 13 Sieved |
| % modified DE | 60 | 60 |
| AFdP @ 15 LPM | 8.05 | 7.94 |
| WFdP @ 0.5 GPM | 14.27 | 14.08 |
| Normalized WFdP to 8" Block | 8.919 | 8.800 |
| Core Block Weight, g | 126.13 | 126.09 |
| Core Block Length, in. | 6.02 | 6.024 |
| Normalized Core wt, g/in. | 20.96 | 20.93 |
| LRV Day2 avg. | 6.50 | 6.60 |
| LRV D2C6 avg. | 6.60 | 6.60 |
| Core Q gal/min | 0.31 | 0.31 |
| Core Length, in. | 5.00 | 5.00 |
| I.D., in. | 0.75 | 0.75 |
| O.D., in. | 2.00 | 2.00 |
| Media Volume, in$^3$ | 13.50 | 13.50 |
| EBCT Sec | 11.3 | 11.3 |

TABLE 14c

| | 1.0" ID | |
|---|---|---|
| | 14-I | 14-J |
| Sleeve | Example 3 | Example 3 |
| Antimicrobial Core | Example 9 Sieved | Example 13 Sieved |

TABLE 14c-continued 1.0" ID

|  | 14-I | 14-J |
|---|---|---|
| % modified DE | 70 | 60 |
| AFdP @ 15 LPM | 7.92 | 7.09 |
| WFdP @ 0.5 GPM | 15.70 | 13.77 |
| Normalized WFdP of 8" Block | 9.813 | 8.606 |
| Core Block Weight, g | 111.66 | 115.1 |
| Core Block Length, in. | 6.02 | 5.99 |
| Normalized Core wt, g/in. | 18.56 | 19.21 |
| LRV Day2 avg. | n/a | 6.57 |
| LRV D2C6 avg. | n/a | 6.40 |
| Core Q, gal/min | 0.31 | 0.31 |
| Core Length, in. | 5.00 | 5.00 |
| I.D., in. | 1.00 | 1.00 |
| O.D., in. | 2.00 | 2.00 |
| Media Volume, in$^3$ | 11.78 | 11.78 |
| EBCT Sec | 9.9 | 9.9 |

TABLE 14d 1.25" ID

|  | 14-K | 14-L |
|---|---|---|
| Sleeve | Example 3 | Example 3 |
| Antimicrobial Core | Example 9 Sieved | Example 13 Sieved |
| % modified DE | 70 | 60 |
| AFdP @ 15 LPM | 5.76 | 5.71 |
| WFdP @ 0.5 GPM | 12.43 | 12.13 |
| Normalized WFdP of 8" Block | 7.769 | 7.581 |
| Core Block Weight, g | 92.80 | 93.85 |
| Core Block Length, in. | 6.02 | 6.02 |
| Normalized Core wt, g/in. | 15.43 | 15.59 |
| LRV Day2 avg. | n/a | 6.10 |
| LRV D2C6 avg. | n/a | 5.23 |
| Core Q, gal/min | 0.31 | 0.31 |
| Core Length, in. | 5.00 | 5.00 |
| I.D., in. | 1.25 | 1.25 |
| O.D., in. | 2.00 | 2.00 |
| Media Volume, in$^3$ | 9.57 | 9.57 |
| EBCT Sec | 8.0 | 8.0 |

TABLE 14e 1.5" ID

|  | 14-M |
|---|---|
| Sleeve | Example 11 |
| Antimicrobial Core | Example 13 Sieved |
| % modified DE | 60 |
| AFdP @ 15 LPM | 3.21 |
| WFdP @ 0.5 GPM | 8.90 |
| Normalized WFdP of 8" Block | 5.563 |
| Core Block Weight, g | 66.88 |
| Core Block Length, in. | 6.02 |
| Normalized Core wt, g/in. | 11.12 |
| LRV Day2 avg. | 4.27 |
| LRV D2C6 avg. | 2.90 |
| Core Q gal/min | 0.31 |
| Core Length, in. | 5.00 |
| I.D., in. | 1.50 |
| O.D., in. | 2.00 |
| Media Volume, in$^3$ | 6.87 |
| EBCT Sec | 5.8 |

The filters of Example 14 show that the formulations and geometries can be varied to meet the needs of desired filter applications while still achieving suitable LRV Day 2 and LRV Day 2, Cycle 6 averages.

Example 15

This example measured the viral reduction capability of a zoned filtration system configured in an annular concentric arrangement of 3 zones. For Example 15, a first zone of carbon block (according to Example 3) was added to protect an anti-microbial core zone (according to Example 13) and a nylon membrane wrap was located around the core zone.

A series of Example 3 carbon blocks were produced, at nominally 10" length. A series of Example 13 blocks were produced according to the Sintered Blocks Procedure, at approximately 8.25" length, then measured for weight and length. Single layer nylon membranes were wrapped around the outer surface of 2" OD, ¾" ID Example 13 blocks. The wrapped cores were inserted into the ID of the Example 3 blocks. The three-zone units were trimmed together at one end on a mitering saw, to create a single face, to which a top end cap was glued. The combination was trimmed again on the mitering saw to a block body length of 5 inches, and the bottom end cap was fitted and glued. Physical characteristics of block weight and length were measured and the measurements for 6 representative blocks are provided in Tables 15a and 15b:

TABLE 15a

|  | Ex. 15-A | Ex. 15-B | Ex. 15-C |
|---|---|---|---|
| O.D., in. | 2.0 | 2.0 | 2.0 |
| I.D., in. | 0.75 | 0.75 | 0.75 |
| Trimmed length, in. | 5.0 | 5.0 | 5.0 |
| Full length, in. | 8.2 | 8.1 | 7.9 |
| Full weight, grams | 192.8 | 189.6 | 188.1 |
| Weight per unit length, g/in. | 23.6 | 23.5 | 23.7 |

TABLE 15b

|  | Ex. 15-D | Ex. 15-E | Ex. 15-F |
|---|---|---|---|
| O.D., in. | 2.0 | 2.0 | 2.0 |
| I.D., in. | 0.75 | 0.75 | 0.75 |
| Trimmed length, in. | 5.0 | 5.0 | 5.0 |
| Full length, in. | 8.2 | 8.1 | 7.9 |
| Full weight, grams | 191.7 | 192.8 | 189.9 |
| Weight per unit length, g/in. | 23.2 | 23.8 | 23.7 |

The nylon membranes had the physical characteristics according to Table 15c:

TABLE 15c

|  | 0.2 μm membrane | 0.8 μm membrane |
| --- | --- | --- |
| Thickness (mils) | 6.8 | 7.5 |
| Forward Flow PL (psi) | 8.7 | 2.9 |
| Bubble Point IL (psi) | 14.3 | 5.3 |

Averaged physical characteristics of three representative combination annular concentric discrete zone filters for each type of membrane are shown in Tables 15d and 15e.

TABLE 15d

|  | Ex. 15-A + 0.2 μm membrane | Ex. 15-B + 0.2 μm membrane | Ex. 15-C + 0.2 μm membrane | Average |
| --- | --- | --- | --- | --- |
| AFdP @ 15 LPM, in. H₂O | 28.3 | 29.3 | 29.4 | 29.0 |
| WFdP @ 0.31 GPM, psi | 37.2 | 37.2 | 37.9 | 37.4 |
| WFdP @ 0.5 GPM, psi | n/a | n/a | n/a | n/a |
| Normalized WFdP (linear) @ 0.5 GPM, dP*in | n/a | n/a | n/a | n/a |

TABLE 15e

|  | Ex. 15-D + 0.8 μm membrane | Ex. 15-E + 0.8 μm membrane | Ex. 15-F + 0.8 μm membrane | Average |
| --- | --- | --- | --- | --- |
| AFdP @ 15 LPM, in. H₂O | 8.2 | 9.1 | 9.0 | 8.8 |
| WFdP @ 0.31 GPM, psi | 9.3 | 11.7 | 10.0 | 10.3 |
| WFdP @ 0.5 GPM, psi | 16.5 | 20.7 | 17.8 | 18.3 |
| Normalized WFdP (linear) @ 0.5 GPM, dP*in | 82.5 | 103.5 | 89.0 | 91.7 |

The wrapped annular concentric discrete 3-zone filters were inserted into AP200 test housings, with no inserts to limit the void volume of the combination housing and block. The MS-2 phage challenge testing was conducted at a 500 mL void volume, at a preset challenge flow rate of 0.31 gpm. The filter devices were challenged with seeded general test water (dechlorinated tap water seeded with $10^6$ platform units per mL (PFU/mL) of MS2) and seeded challenged test water (dechlorinated water, humic acid, and seeded with $10^6$ PFU/mL of MS2). FD means flow decay. The samples using the 0.8 μm membrane plugged before the 75% initial flow sample. Results are shown in Tables 15f and 15 g.

TABLE 15f

| Cycle | Inlet (PFU/mL) | Ex. 15-A + 0.2 μm membrane (PFU/mL) | LRV | Ex. 15-B + 0.2 μm membrane (PFU/mL) | LRV | Ex. 15-C + 0.2 μm membrane (PFU/mL) | LRV |
| --- | --- | --- | --- | --- | --- | --- | --- |
| 1 | ND | ND | — | ND | — | ND | — |
| 7 | 2.6E+6 | ND | 6.4 | ND | 6.4 | ND | 6.4 |
| 9 | 4.9E+3 | ND | — | ND | — | ND | — |
| 14 | 9.5E+6 | FD | FD | FD | FD | FD | FD |
| 15 | 2.7E+5 | — | — | — | — | — | — |

TABLE 15g

| Cycle | Inlet (PFU/mL) | Ex. 15-D + 0.8 μm membrane (PFU/mL) | LRV | Ex. 15-E + 0.8 μm membrane (PFU/mL) | LRV | Ex. 15-F + 0.8 μm membrane (PFU/mL) | LRV |
| --- | --- | --- | --- | --- | --- | --- | --- |
| 1 | ND | ND | — | ND | — | ND | — |
| 7 | 2.6E+6 | ND | 6.4 | ND | 6.4 | ND | 6.4 |
| 9 | 4.9E+3 | ND | — | ND | — | ND | — |
| 14 | 9.5E+6 | ND | 7.0 | ND | 7.0 | ND | 7.0 |
| 15 | 2.7E+5 | ND | — | ND | — | ND | — |

The nominal nylon membrane grades in all cases provided a failsafe for the antimicrobial core, which caused a diminishment to flow prior to core antiviral exhaustion. Effective MS-2 adsorption was demonstrated by an LRV rating of greater than 4.0 at each tested point in the challenge cycle.

Example 16

This example measured the viral reduction capability of a zoned filtration system configured in an annular concentric arrangement of 3 zones. For Example 16, a first zone of carbon block (according to Example 3) was added to protect an anti-microbial core zone (according to Example 13) and a nylon membrane wrap was located around the outer surface of the carbon core.

A series of Example 3 carbon blocks were produced, at nominally 10" length. A series of Example 13 blocks were produced according to the Sintered Blocks Procedure, at approximately 7.5" length, then measured for weight and length. The 2" OD, ¾" ID Example 13 blocks were inserted into the ID of the Example 3 blocks. A single layer nylon membrane was wrapped around the outer surface of each carbon. The three-zone units were trimmed together at one end on a mitering saw, to create a single face, to which a top end cap was glued. The combination was trimmed again on the mitering saw to a block body length of 5 inches, and the bottom end cap was fitted and glued. Physical characteristics of block weight and length were measured and the measurements for 6 representative blocks are provided in Tables 16a and 16b:

TABLE 16a

|  | Ex. 16-A | Ex. 16-B | Ex. 16-C |
| --- | --- | --- | --- |
| O.D., in. | 2.0 | 2.0 | 2.0 |
| I.D., in. | 0.75 | 0.75 | 0.75 |
| Trimmed length, in. | 5.0 | 5.0 | 5.0 |
| Full length, in. | 8.4 | 8.1 | 7.9 |
| Full weight, grams | 202.1 | 193.9 | 188.6 |
| Weight per unit length, g/in. | 23.9 | 23.8 | 23.8 |

TABLE 16b

|  | Ex. 16-D | Ex. 16-E | Ex. 16-F |
| --- | --- | --- | --- |
| O.D., in. | 2.0 | 2.0 | 2.0 |
| I.D., in. | 0.75 | 0.75 | 0.75 |
| Trimmed length, in. | 5.0 | 5.0 | 5.0 |
| Full length, in. | 8.3 | 8.0 | 8.1 |
| Full weight, grams | 195.8 | 189.1 | 191.5 |
| Weight per unit length, g/in. | 23.7 | 23.7 | 23.7 |

The nylon membranes had the physical characteristics according to Table 15c above.

Averaged physical characteristics of three representative combination annular concentric discrete zone filters for each type of membrane are shown in Tables 16c and 16d.

TABLE 16c

|  | Ex. 16-A + 0.2 μm membrane | Ex. 16-B + 0.2 μm membrane | Ex. 16-C + 0.2 μm membrane | Average |
|---|---|---|---|---|
| WFdP @ 0.31 GPM, psi | 31.5 | 33.6 | 32.8 | 32.6 |
| WFdP @ 0.5 GPM, psi | 55.0 | 56.1 | 55.4 | 55.5 |
| Normalized WFdP (linear) @ 0.5 GPM, dP*in | 275.0 | 280.5 | 277.0 | 277.5 |

TABLE 16d

|  | Ex. 16-D + 0.8 μm membrane | Ex. 16-E + 0.8 μm membrane | Ex. 16-F + 0.8 μm membrane | Average |
|---|---|---|---|---|
| WFdP @ 0.31 GPM, psi | 10.2 | 10.0 | 11.5 | 10.6 |
| WFdP @ 0.5 GPM, psi | 18.1 | 16.5 | 18.9 | 17.8 |
| Normalized WFdP (linear) @ 0.5 GPM, dp*in | 90.5 | 82.5 | 94.5 | 89.2 |

The filter devices were challenged as described in Example 15. Results are shown in Tables 16e and 16f.

TABLE 16e

| Cycle | Inlet (PFU/mL) | Ex. 16-A + 0.2 μm membrane (PFU/mL) | LRV | Ex. 16-B + 0.2 μm membrane (PFU/mL) | LRV | Ex. 16-C + 0.2 μm membrane (PFU/mL) | LRV |
|---|---|---|---|---|---|---|---|
| 1 | ND | ND | — | ND | — | ND | — |
| 7 | 2.0E+6 | ND | 6.3 | ND | 6.3 | ND | 6.3 |
| 9 | 2.9E+4 | ND | — | ND | — | ND | — |
| 14 | FD | FD | FD | FD | FD | FD | FD |
| 15 | ND | ND | — | ND | — | ND | — |

TABLE 16f

| Cycle | Inlet (PFU/mL) | Ex. 16-D + 0.8 μm membrane (PFU/mL) | LRV | Ex. 16-E + 0.8 μm membrane (PFU/mL) | LRV | Ex. 16-F + 0.8 μm membrane (PFU/mL) | LRV |
|---|---|---|---|---|---|---|---|
| 1 | ND | ND | — | ND | — | ND | — |
| 7 | 2.0E+6 | ND | 6.3 | ND | 6.3 | ND | 6.3 |
| 9 | 2.9E+4 | ND | — | ND | — | ND | — |
| 14 | FD | FD | FD | FD | FD | FD | FD |
| 15 | ND | — | — | — | — | — | — |

The nominal nylon membrane grades in all cases provided a failsafe for the antimicrobial core, which caused a diminishment to flow prior to core antiviral exhaustion. Effective MS-2 adsorption was demonstrated by an LRV rating of greater than 4.0 at each tested point in the challenge cycle.

The arrangement of annular concentric filtration zones of Example 16, optimized for discrete filtration elements per location, provided continuous microbial reductive capacities until such point that the colloidal portion of the polyanionic acid contaminant clogged the membrane zone of the 3-zone filtration unit.

The addition of a third filtration zone moderately increased differential pressure values, depending on the membrane pore size, compared to filters without the membranes. Optimization of membrane pore size could offer the benefit of tailoring filtration characteristics yielding the highest levels of efficiency and filter reliability, while enhancing protection of downstream mechanisms in multizone sequential units.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

While the articles, apparatus and methods for making the articles contained herein constitute preferred embodiments of the disclosure, it is to be understood that the disclosure is not limited to these precise articles, apparatus and methods, and that changes may be made therein without departing from the scope of the disclosure which is defined in the appended claims.

What is claimed is:

1. A separation matrix comprising:
   a surface-modified inorganic component; and
   a polymeric binder comprising particles having an irregular, convoluted surface;
   wherein the surface-modified inorganic component comprises a reaction product of an anti-microbial component comprising a quaternary ammonium salt containing an epoxide group and an inorganic component, and thereby comprising a covalent bond directly between the quaternary ammonium cation and the inorganic component.

2. The matrix of claim 1, wherein the polymeric binder comprises ultra high molecular weight polyethylene.

3. The matrix of claim 1 wherein the polymeric binder further comprises particles having a generally spherical, non-porous structure.

4. The matrix of claim 1, wherein the particles having the irregular, convoluted surface have an average particle size in the range of 10 to 100 microns.

5. The matrix of claim 3, wherein the particles having the generally spherical, non-porous structure have an average particle size in the range of 10 to 100 microns.

6. The matrix of claim 1, wherein the quaternary ammonium salt containing the epoxide group has the formula according to I:

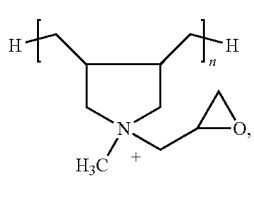

I wherein n is in the range of 3 to 250.

7. The matrix of claim 6, wherein n is in the range of 5 to 24.

8. The matrix of claim 1, wherein the surface-modified inorganic component is present in an amount in the range of 60 to 85% by weight and the polymeric binder is present in an amount in the range of 15 to 40% by weight.

9. The matrix of claim 3, wherein the polymeric binder comprises ultra high molecular weight polyethylene, the particles comprising the irregular, convoluted surface being present in an amount in the range of 10 to 40% by weight of the matrix, and the particles having the generally spherical, non-porous structure being present in an amount of up to 40% by weight of the matrix.

10. The matrix of claim 1, wherein the surface-modified inorganic component has a positive zeta potential at a pH of 9 or greater.

11. The matrix of claim 1, wherein the inorganic component is diatomaceous earth.

12. The matrix of claim 1 being effective to provide at least a 4 log reduction of MS-2 phage.

13. The matrix of claim 12, wherein the reduction occurs over a service life of the matrix.

14. The matrix of claim 13, wherein the reduction occurs up to a point of physical plugging of the matrix.

15. The matrix of claim 1, which is free of a cationic metal salt pretreatment.

16. The matrix of claim 1 further comprising carbon particles having an average diameter of 100 μm.

17. A filter element comprising:
a housing and a separation matrix located therein;
the separation matrix comprising a surface-modified inorganic component and an ultra high molecular weight polyethylene polymeric binder;
wherein the surface-modified inorganic component comprises a reaction product of an anti-microbial component according to formula I:

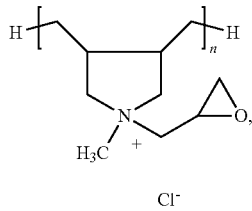

wherein n is in the range of 5 to 24 and diatomaceous earth and comprises a covalent bond directly between the cation of formula I and the diatomaceous earth; and
wherein the ultra high molecular weight polyethylene comprises particles having an irregular, convoluted surface.

18. The filter element of claim 17, wherein the particles having the irregular, convoluted surface have an average particle size in the range of 10 to 100 microns.

19. A method of making a sintered porous article, the method comprising:
providing a base material of diatomaceous earth in a processing tank;
providing an anti-microbial component comprising a quaternary ammonium salt containing an epoxide group;
agitating the base material in the processing tank substantially simultaneously with spraying the anti-microbial component into the processing tank to form a coated base material;
maintaining a ratio of the anti-microbial component to the base material such that the coated base material is below its compaction point;
drying the coated base material under vacuum;
activating the coated base material, thereby forming a covalent bond between the quaternary ammonium cation and the diatomaceous earth to provide a surface-modified inorganic component;
mixing a polymeric binder comprising particles having an irregular, convoluted surface with the surface-modified inorganic component;
filling a mold with the mixture of the particles having an irregular, convoluted surface and the surface-modified inorganic component to form a matrix; and
heating the matrix to point-weld the polymeric binder to the surface-modified inorganic component and to form the porous sintered article.

20. The method of claim 19, wherein the polymeric binder comprises ultra high molecular weight polyethylene.

21. The method of claim 19, wherein the quaternary ammonium salt containing the epoxide group comprises a compound according to formula I:

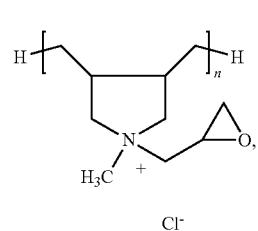

wherein n is in the range of 5 to 24.

22. A separation media comprising activated carbon and a reaction product of a quaternary ammonium salt containing an epoxide group having the formula according to I:

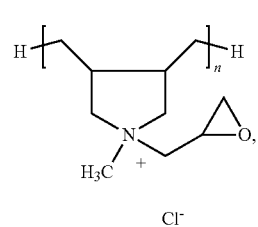

wherein n is in the range of 3 to 250 and diatomaceous earth, wherein the reaction product has a covalent bond directly between the quaternary ammonium cation and the diatomaceous earth.

23. The separation media of claim 22, wherein n is in the range of 5 to 24, and wherein the reaction product maintains a positive zeta potential for at least one month.

24. A method of filtering water comprising providing a filter matrix comprising a surface-modified inorganic component; and a polymeric binder comprising particles having an irregular, convoluted surface; wherein the surface-modified inorganic component comprises a reaction product of an anti-microbial component comprising a quaternary ammonium salt containing an epoxide group and an inorganic component, and thereby comprising a covalent bond directly between the quaternary ammonium cation and the inorganic component; and passing water through the matrix.

25. A filtration system comprising at least a first zone and a second zone, wherein the first zone comprises:

a surface-modified inorganic component; and
a polymeric binder comprising particles having an irregular, convoluted surface;
wherein the surface-modified inorganic component comprises a reaction product of an anti-microbial component comprising a quaternary ammonium salt containing an epoxide group and an inorganic component, and thereby comprises a covalent bond directly between the quaternary ammonium cation and the inorganic component.

26. The system of claim 25, wherein the second zone comprises a surface sieve, a depth sieve, a chemical adsorption matrix, a chelation matrix, a catalytic matrix, or combinations thereof.

27. The system of claim 25, wherein the first zone and the second zone are annularly concentrically disposed to each other.

28. The system of claim 27 wherein the second zone surrounds the first zone.

29. The system of claim 25, wherein the first zone and the second zone are layered.

30. The system of claim 29, wherein the second zone is located at an upstream portion of the filtration system and the first zone is located at a downstream portion of the filtration system.

31. The system of claim 25, wherein the polymeric binder comprises ultra high molecular weight polyethylene.

32. The system of claim 25, wherein the polymeric binder further comprises particles having a generally spherical, non-porous structure.

33. The system of claim 25 wherein the particles having the irregular, convoluted surface have an average particle size in the range of 10 to 100 microns.

34. The system of claim 25, wherein the quaternary ammonium salt containing the epoxide group has the formula according to I:

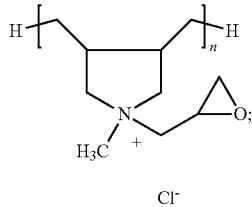

wherein n is in the range of 3 to 250.

35. The system of claim 34, wherein n is in the range of 5 to 24.

36. A filtration system comprising a first concentric zone and a second concentric zone surrounding the first concentric zone,
the first zone comprising:
a surface-modified inorganic component and a first polymeric binder comprising particles having an irregular, convoluted surface;
wherein the surface-modified inorganic component comprises a reaction product of an anti-microbial component comprising a quaternary ammonium salt containing an epoxide group and an inorganic component, and thereby comprises a covalent bond directly between the quaternary ammonium cation and the inorganic component; and
the second zone comprising an adsorptive component and a second polymeric binder.

37. The system of claim 36, wherein the second polymeric binder comprises particles having an irregular, convoluted surface.

38. The system of claim 36, wherein the first polymeric binder comprises ultra high molecular weight polyethylene.

39. The system of claim 36, wherein the adsorptive component of the second zone comprises activated carbon and the second polymeric binder comprises ultra high molecular weight polyethylene.

40. The system of claim 36, further comprising a third zone surrounding the second zone, wherein the third zone comprises a surface sieve.

41. The system of claim 36, further comprising a third zone surrounding the first zone, wherein the first zone comprises a surface sieve.

42. A method of making a filtration system, the method comprising:
providing a base material of diatomaceous earth in a processing tank;
providing an anti-microbial component comprising a quaternary ammonium salt containing an epoxide group;
agitating the base material in the processing tank substantially simultaneously with spraying the anti-microbial component into the processing tank to form a coated base material;
maintaining a ratio of the anti-microbial component to the base material such that the coated base material is below its compaction point;
drying the coated base material under vacuum, thereby forming a covalent bond between the quaternary ammonium cation and the diatomaceous earth to provide a surface-modified inorganic component;
mixing a first polymeric binder with the surface-modified inorganic component to form a first matrix;
heating the first matrix to point-weld the first polymeric binder to the surface-modified inorganic component and to form a first filtration zone;
providing a second filtration zone comprising a second polymeric binder, and a chemical adsorption matrix; and
locating the first filtration zone adjacent to the second filtration zone to form the filtration system.

43. The method of claim 42, wherein the second filtration zone is concentric with the first filtration zone.

44. The method of claim 42, wherein the quaternary ammonium salt containing the epoxide group comprises a compound according to formula I:

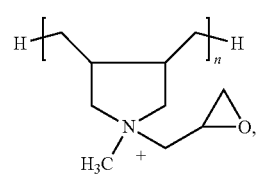

wherein n is in the range of 5 to 24.

45. A method of filtering water comprising providing a filtration system comprising at least a first zone and a second zone, wherein the first zone comprises: a surface-modified inorganic component; and a polymeric binder comprising particles having an irregular, convoluted surface; wherein the surface-modified inorganic component comprises a reaction product of an anti-microbial component comprising a quaternary ammonium salt containing an epoxide group and an inorganic component, and thereby comprises a covalent bond directly between the quaternary ammonium cation and the inorganic component; and passing water through the filtration system.

\* \* \* \* \*

UNITED STATES PATENT AND TRADEMARK OFFICE
CERTIFICATE OF CORRECTION

| | | |
|---|---|---|
| PATENT NO. | : 8,453,849 B2 | Page 1 of 1 |
| APPLICATION NO. | : 12/744392 | |
| DATED | : June 4, 2013 | |
| INVENTOR(S) | : Thomas Joseph Hamlin | |

It is certified that error appears in the above-identified patent and that said Letters Patent is hereby corrected as shown below:

On the Title Page of the Patent, in Column 1, item (75), under "(Inventors)"
Lines 5-6, delete "Tuscon, AZ (US);" and insert -- Tucson, AZ (US); --, therefor.

In the Specification

Column 8
Line 47, delete "S 1000" and insert -- S1000 --, therefor.

Column 10
Line 56, delete "application" and insert -- application. --, therefor.

Column 12
Line 44, delete "electokinetically" and insert -- electrokinetically --, therefor.

Column 14
Line 14, delete "though" and insert -- through --, therefor.
Line 25, delete "dichlorinated" and insert -- dechlorinated --, therefor.

Signed and Sealed this
Eighth Day of October, 2013

Teresa Stanek Rea
*Deputy Director of the United States Patent and Trademark Office*